US008986358B2

(12) United States Patent
Svanberg et al.

(10) Patent No.: US 8,986,358 B2
(45) Date of Patent: Mar. 24, 2015

(54) SYSTEM AND METHOD FOR CONTROLLING AND ADJUSTING INTERSTITIAL PHOTODYNAMIC LIGHT THERAPY PARAMETERS

(75) Inventors: Sune Svanberg, Lund (SE); Johan Axelsson, Lund (SE); Johannes Swartling, Lund (SE); Ann Johansson, Lund (SE); Stefan Andersson-Engels, Lund (SE)

(73) Assignee: Spectracure AB, Lund (SE)

(*) Notice: Subject to any disclaimer, the term of this patent is extended or adjusted under 35 U.S.C. 154(b) by 1640 days.

(21) Appl. No.: 12/377,595

(22) PCT Filed: Aug. 15, 2007

(86) PCT No.: PCT/EP2007/058477
§ 371 (c)(1),
(2), (4) Date: Oct. 29, 2010

(87) PCT Pub. No.: WO2008/020050
PCT Pub. Date: Feb. 21, 2008

(65) Prior Publication Data
US 2011/0034971 A1    Feb. 10, 2011

Related U.S. Application Data

(60) Provisional application No. 60/837,751, filed on Aug. 15, 2006, provisional application No. 60/883,738, filed on Jan. 5, 2007, provisional application No. 60/942,630, filed on Jun. 7, 2007.

(51) Int. Cl.
*A61N 5/06* (2006.01)
*A61B 17/00* (2006.01)
(Continued)

(52) U.S. Cl.
CPC .............. *A61N 5/062* (2013.01); *A61N 5/0601* (2013.01); *A61B 2017/00022* (2013.01); *A61B 2018/00642* (2013.01); *A61B 2019/505* (2013.01); *A61N 2005/0612* (2013.01); *A61N 2005/063* (2013.01)
USPC ............................................. 607/88; 607/92

(58) Field of Classification Search
USPC ...................................................... 607/88–92
See application file for complete search history.

(56) References Cited

U.S. PATENT DOCUMENTS

| 5,292,320 A | 3/1994 | Brown et al. |
| 5,527,349 A | 6/1996 | Landry et al. |

(Continued)

FOREIGN PATENT DOCUMENTS

| EP | 1 334 748 A | 8/2003 |
| EP | 1 470 837 A | 10/2004 |

(Continued)

OTHER PUBLICATIONS

Censor et al., "On the use of Cimmino's simultaneous projections method for computing a solution of the inverse problem in radiation therapy treatment planning", 1988.*

(Continued)

*Primary Examiner* — Ahmed Farah
(74) *Attorney, Agent, or Firm* — Knobbe, Martens, Olson & Bear LLP

(57) ABSTRACT

A method and system for controlling and adjusting light in interstitial photodynamic light therapy (IPDT) in a subject is disclosed. More particularly, a method for controlling the light in interstitial tumor photodynamic light therapy is described using a calculation method for determination of status of tissue during the PDT treatment. The status is used in a feedback loop to control the continued PDT treatment. Methods are disclosed that constitute pre-treatment and real-time dosimetry modules for IPDT on the whole prostate glandular tissue. The method includes reconstruction of the target geometry, optimization of source fiber positions within this geometry, monitoring of the light attenuation during the treatment procedure and updating individual fiber irradiation times to take into account any variation in tissue light transmission. A control device that is arranged to restrict delivery of therapeutic light treatment at least temporary in dependence of at least one attribute of one of photodynamic treatment parameters. In comparison to no treatment feedback, a significant undertreatment of the patient as well as damage to healthy organs at risk are avoided.

25 Claims, 14 Drawing Sheets

(51) Int. Cl.
*A61B 18/00* (2006.01)
*A61B 19/00* (2006.01)

(56) References Cited

U.S. PATENT DOCUMENTS

| | | | |
|---|---|---|---|
| 6,138,046 | A | 10/2000 | Dalton |
| 6,366,719 | B1 | 4/2002 | Heath et al. |
| 7,037,325 | B2 | 5/2006 | Svanberg et al. |
| 7,988,715 | B2 | 8/2011 | Johansson et al. |
| 2004/0267335 | A1 | 12/2004 | Tulip et al. |
| 2006/0282132 | A1* | 12/2006 | Arai et al. ............ 607/88 |
| 2006/0282136 | A1 | 12/2006 | Tulip et al. |
| 2007/0282404 | A1 | 12/2007 | Cottrell et al. |
| 2008/0033339 | A1 | 2/2008 | Tulip et al. |
| 2008/0221647 | A1 | 9/2008 | Chamberland et al. |

FOREIGN PATENT DOCUMENTS

| | | | |
|---|---|---|---|
| EP | 1 637 182 A | | 3/2006 |
| WO | WO 99/06113 A | | 2/1999 |
| WO | WO 01/97902 A2 | | 12/2001 |
| WO | WO 03/041575 A1 | | 5/2003 |
| WO | WO 2004/030761 A1 | | 4/2004 |
| WO | WO 2004-112902 | | 12/2004 |
| WO | WO 2008/020050 A1 | | 2/2008 |
| WO | WO 2008/062000 | | 5/2008 |
| WO | WO 2008/103982 A2 | | 8/2008 |
| WO | WO 2008/152076 A2 | | 12/2008 |

OTHER PUBLICATIONS

Altschuler et al., "Optimized Interstitial PDT Prostate Treatment Planning with the Cimmino Feasibility Algorithm," Medical Physics, AIP, vol. 32, No. 12, Nov. 9, 2005.

International Search Report and Written Opinion issued in PCT Application No. PCT/EP2010/051605 dated May 7, 2010.

Weersink, et al.,"Techniques for Delivery and Monitoring of TOOKAD (WST09)—Mediated Photodynamic Therapy of the Prostate: Clinical Experience and Practicalities", Proceedings of the SPIE, The International Society for Optical Engineering, vol. 5689, No. 1, (2005), pp. 112-122.

Johansson et al., "System for Integrated Interstitial Photodynamic Therapy and Dosimetric Monitoring", Proceedings of the SPIE—The International Society for Optical Engineering, vol. 5689, No. 1, (2005), pp. 130-140.

Johnansson et al., "In vivo Measurement of Parameters of Dosimetric Importance during Interstitial Photodynamic Therapy of Thick Skin Tumors", Journal of Biomedical Optics SPIE USA, vol. 11, No. 3, (May 2005), pp. 34029-34031.

Andersson-Engels et al., "Integrated System for Interstitial Photodynamic Therapy", Proceedings of SPIE—The International Society for Optical Engineering SPIE-Int. Soc Opt Eng USA, vol. 5123, (2003), pp. 293-302.

Svensson et al., "In vivo Optical Characterization of Human Prostate Tissue Using Near-Infrared Time-Resolved Spectroscopy", Journal of Biomedical Optics SPIE USA, vol. 12, No. 1, (Jan. 2007) pp. 14022-14031.

Dougherty et al., "Photodynamic Therapy", Journal of the National Cancer Institute, vol. 90, No. 12, (Jun. 17, 1998), pp. 889-905.

Johansson et al., "Realtime Light Dosimetry Software Tools for Interstitial Photodynamic Therapy of the human Prostrate", Medical Physics, AIP, Melville, NY , US, vol. 34, No. 11, (Oct. 19, 2007), pp. 4309-4321.

\* cited by examiner

SYSTEM AND METHOD FOR CONTROLLING AND ADJUSTING INTERSTITIAL PHOTODYNAMIC LIGHT THERAPY PARAMETERS

CROSS REFERENCE TO RELATED APPLICATIONS

This application claims priority to U.S. Provisional Application 60/837,751 filed on Aug. 15, 2006, to U.S. Provisional Application 60/883,738 filed on Jan. 5, 2007, and to U.S. Provisional Application 60/942,630 filed on Jun. 7, 2007.

FIELD OF THE INVENTION

This invention pertains in general to the field of photodynamic light therapy (PDT) and related systems, devices, computer program products and methods. More particularly the invention relates to controlling and adjusting of light in such a PDT system. Even more particularly, the invention refers to a system and method for controlling light in an interstitial tumor PDT system.

BACKGROUND OF THE INVENTION

Photodynamic therapy (PDT) is a cancer treatment modality that has shown promising results in terms of selectivity and efficacy, see e.g. Dougherty T J, et. al.: Photodynamic therapy, Journal of the National Cancer Institute 1998; 90: 889-905.

PDT relies on the use of a photosensitizer agent being activated by light in the presence of oxygen, leading to the production of toxic singlet oxygen radicals. Tissue destruction results from apoptosis, necrosis and vascular damage caused by these toxic singlet oxygen radicals, see e.g. Noodt B B, et. al.: Apoptosis and necrosis induced with light and 5-aminolaevulinic acid-derived protoporphyrin IX, British Journal of Cancer 1996; 74: 22-29.

A limited penetration in the tissue of the activating light is a general issue of PDT. Only tumors less than about 5 mm in thickness may be treated by surface irradiation. In order to treat thicker and/or deeper lying tumors, interstitial PDT may be utilized. In interstitial PDT, light-conducting optical fibers are brought into the tumor using, e.g., a syringe needle, in the lumen of which a fiber has been placed, which is for instance described in PCT/SE2006/050120 of the same applicant as the present application.

In order to achieve an efficient treatment, several fibers have been used to ascertain that all tumor cells are subjected to a sufficient dose of radiation so that the toxic singlet state is obtained. In the Swedish patent SE 503408 an interstitial PDT system is described, where six fibers are used for treatment as well as for measurement of the light flux which reaches a given fiber in the penetration through the tissue from the other fibers. According to the disclosure of SE 503408, the light from a single laser is divided into six different parts using a beamsplitter system comprising a large number of mechanical and optical components. The light is then focused into each of the six individual treatment fibers. One fiber is used as a transmitter while the other fibers are used as receivers of radiation penetrating the tissue. The interstitial PDT system disclosed in SE503408 allows feedback from light scattering but the document does not disclose any information or gives guidance concerning parameters of importance for controlling and adjusting light therapy or a need therefor.

To optimize the biological effect in interstitial PDT, an accurate dosimetry method is needed. For instance a fixed light dose may be used, and radiance at a therapeutic wavelength of the therapeutic light used may be kept constant throughout the PDT treatment. Furthermore, the illumination time may be determined by a requirement to deliver a predetermined incident light dose, expressed in $J/cm^2$. Such a simplified dose metric ignores changes of treatment conditions during PDT treatment. For instance, such changes may comprise treatment-induced variations of tissue light transmission, variations of sensitizer concentration, and varying tissue oxygenation status throughout the target tissue to be treated by PDT. Amongst other things, such variations might explain the highly variable PDT effect observed. For instance a recurrence rate displays large variations despite equivalent light dose, as shown in Calzavara-Pinton PG: Repetitive photodynamic therapy with topical $\alpha$-aminolaevulinic acid as an appropriate approach to the routine treatment of superficial non-melanoma skin tumors, Journal of Photochemistry and Photobiology B: Biology 1995; 29: 53-57. Moreover, necrotic volume displays large variations despite equivalent light dose, according to Curnow A et. al.: Oxygen monitoring during 5-aminolaevulinic acid induced photodynamic therapy in normal rat colon, Comparison of continuous and fractionated light regimes, Journal of Photochemistry and Photobiology B: Biology 2000; 58: 149-155.

EP 1470837 of Tulip et. al. discloses a switched photodynamic therapy apparatus and method. A photodynamic therapy apparatus and method are described in which a phototoxic drug is supplied to an arterical supply of a target tissue, and delivery of drug activating light to target tissue through probes is controlled by sequential selection of operation of the probes. Furthermore, an automatic radiance probe is used for efficient optical characterization of target tissue and optical dose is monitored by sequential selection of probes as transmitters and receivers. However, the apparatus and method are not providing an efficiency feedback of the therapy delivered. Furthermore, the disclosure lacks a practical guidance of how and when to control light delivery as the probes are operated sequentially at a fixed, predetermined rate. Moreover, a specific rotational probe has to be used for measuring tissue characteristics of a treatment site, which appears practically difficult to implement in a clinical environment.

Hence, there is a need for an advantageous method and/or system for controlling and adjusting light therapy and/or related parameters during PDT in vivo or in vitro.

SUMMARY OF THE INVENTION

Accordingly, embodiments of the present invention preferably seeks to mitigate, alleviate or eliminate one or more deficiencies, disadvantages or issues in the art, such as the above-identified, singly or in any combination by providing a system, a method, a computer program, a computer program, and a medical workstation according to the appended patent claims.

Even more particularly, the invention comprises a method, wherein the method incorporates a calculation method for determination of a status of tissue during the PDT treatment. The calculation method is based on an evaluation of at least one parameter related to the tumor or to a sensitizer. A method for controlling the light-treatment is also disclosed where the total treatment time is determined from either the sensitizer concentration, fluence rate or from the tissue oxygenation.

According to a first aspect of the invention, a system for providing interstitial photodynamic therapy on tissue in a body is provided. The system comprises at least one optical fiber for delivering a therapeutic light to said tissue for interaction with a photosensitizer agent in said tissue, wherein said optical fiber is devised to be interstitially inserted into said tissue with a distal end region thereof; a device for evaluating at least one photodynamic treatment parameter of said interstitial photodynamic therapy at said distal end region of said optical fiber; a device for modifying characteristics of said therapeutic light of said interstitial photodynamic therapy in response to the evaluation of said photodynamic treatment parameter; and a control device that is arranged to restrict said delivery of therapeutic light treatment at least temporary in dependence of at least one attribute of one of said photodynamic treatment parameters.

According to another aspect of the invention, a computer program for processing by a computer is provided. The computer program comprises code segments for controlling and adjusting light therapy in a photodynamic treatment of a subject, in a system for providing interstitial photodynamic therapy on tissue in a body. The computer program comprises a first code segment for evaluating at least one photodynamic treatment parameter of said interstitial photodynamic therapy at said distal end region of said optical fiber; a second code segment for modifying characteristics of said therapeutic light of said interstitial photodynamic therapy in response to the evaluation of said photodynamic treatment parameter; and a third code segment for restricting said delivery of therapeutic light treatment at least temporary in dependence of at least one attribute of one of said photodynamic treatment parameters.

According to a further aspect of the invention, a medical workstation is provided that is configured for running the computer program of the aforementioned aspect of the invention for interstitial photodynamic therapy.

According to an embodiment of the invention, a calculation method for monitoring and adjusting treatment parameters during photodynamic light therapy is disclosed. A light dose distribution from measured parameters is obtained and a correction of light delivery conditions from said parameters may be used to control the therapy.

According to one embodiment, the invention relates to a method for controlling and adjusting the light therapy in a photodynamic treatment of a subject. The method may be performed in-vivo or in-vitro, and comprises the steps:

a) providing at least one therapy light emitting source for therapy, said source being adapted to be inserted interstitially within the tissue site, said source having means for controlling the light dose thereof;

b) providing at least one determination light emitting source, said source being adapted to be inserted interstitially within the tissue site and being adapted to determine a tissue status or sensitizer parameter;

c) determining directly or indirectly at least one parameter related to tissue status or sensitizer;

d) calculating a light dose distribution from measured parameters and a correction of light delivery conditions from said parameters;

e) repeating said determining (c) and calculating (d) until at least one of said parameters has reached a predetermined level; and thereupon f) terminating said photodynamic treatment at least partly.

The method starts with measuring and calculating initial parameter values and threshold levels, which is then converted to light delivery conditions for the treatment. This means that the time and power for every light emitting source used in the therapy is set during the time interval in which the light emitting source is on. The parameters related to tissue status or sensitizer during the treatment are then measured in real-time and a new calculation will give new light delivery conditions.

Further embodiments of the invention are defined in the dependent claims, wherein features for the second and subsequent aspects of the invention are as for the first aspect mutatis mutandis.

Some embodiments of the invention provide for avoidance of an undertreatment of a patient. Some embodiments of the invention also provide for increased patient safety by avoiding damage to healthy organs at risk.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
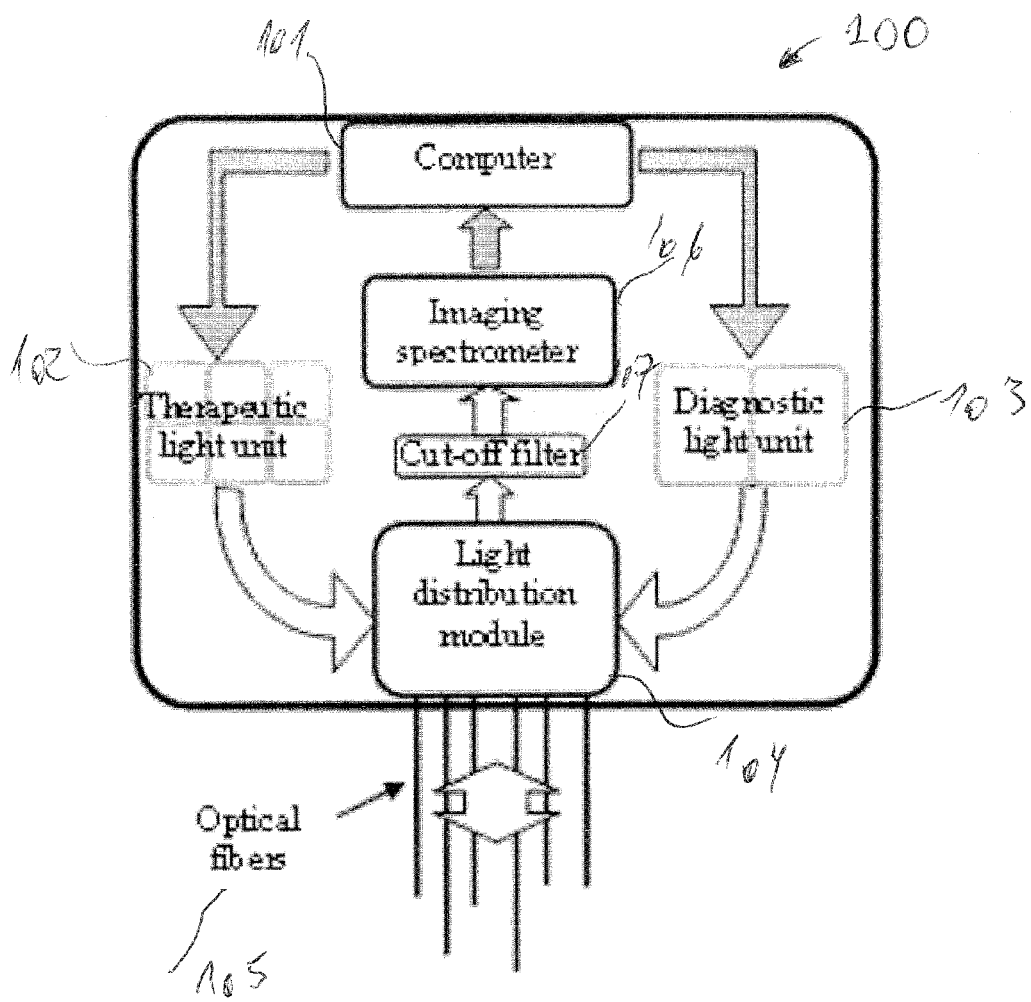
FIG. 1 is a schematic drawing of an interstitial PDT apparatus.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to a PDT system and method, and in particular to an interstitial PDT system and method with reference to an embodiment of treatment of prostate cancer. However, it will be appreciated that the invention is not limited to this application but may be applied to many other organs, including for example liver, oesophagus, pancreas, breast, brain, lung, trachea, eye, urinary tract, brain stem, spinal marrow, bone marrow, kidneys, stomach, intestines, pancreas, gall bladder, etc.

Photodynamic therapy (PDT) has become a clinically more accepted method for treating certain types of malignancies in various organs, partly due to advantages, such as the possibility of repeated treatment and restriction of the treatment-induced tissue damage to irradiated sites. The PDT effect is caused by a combination of treatment induced apoptosis and direct necrosis, vascular damage and possibly an elicited immune response, where the extent of tissue damage depends on the light dose, the tissue oxygenation and the sensitizer concentration. For PDT, clinical treatment protocols often rely on a light threshold model. This simplified model is based on the assumption that only tissue regions exposed to a light dose exceeding a pre-defined threshold are damaged. The threshold light dose is likely to depend on tissue type and photosensitizer used. From the point of view of the deposited light dose, it is essential to monitor the tissue optical properties before and during the PDT treatment. significant inter- and intra-patient variations of the absorption and scattering coefficients of prostate tissue have been measured by many groups. In addition, any treatment-induced variations in absorption and scattering, possibly due to changes in blood content and tissue oxygenation status, directly influence the light distribution during the course of the treatment. Clearly, there is a need to monitor the tissue optical properties in individual patients both before and during the treatment.

Recently, several groups have proved PDT a successful alternative for the treatment of prostate cancer. Bown et al. have used the photosensitizer mTHPC for treating secondary and primary prostate cancer. The light doses were 20-100 J per treatment site, resulting in significant treatment-induced necrosis and decreasing PSA levels. Complications following treatment included transitory irritative voiding symptoms, stress incontinence and one case of impaired sexual function. According to the authors, a more detailed drug and light dosimetry might lead to better discrimination between target tissue and surrounding sensitive organs. Weersink et al. have reported on treatment of recurrent prostate cancer using the vascular targeted photosensitizer Tookad, (WST09). During a Phase I clinical trial both light (100-360 J/cm) and drug ($\leq 2$ mg/kg) dose-escalation studies have been carried out. At the maximum drug dose, lesion formation was observed to primarily depend on light dose. Furthermore, Hahn et al. have utilized the photosensitizer Motexafin Lutetium for the treatment of recurrent prostate carcinoma in combination with monitoring of light fluence, drug level and oxygen distribution. In common for the different PDT-trials on prostate tissue were the large intra and inter-patient variations in treatment-induced necrotic volumes despite delivering similar drug and light doses. These variations can possibly be due to biological differences in tissue composition and short-term treatment response, directly influencing the light distribution within the prostate tissue.

Some parameters that play a role in dosimetry in PDT comprise the fluence rate distribution, the sensitizer concentration, the blood flow, the temperature, and the tissue oxygenation within the volume of interest. Although some of these parameters are known, a method for controlling and adjusting such light therapy parameters, is not known.

During photodynamic therapy significantly decreased tissue light transmission may occur, which may be explained by increase in tissue average blood content and tissue de-oxygenation. In the end, the absorption increase affects light penetration and limits the treatment volume. Also, a good oxygen supply to the PDT treatment site is necessary for a positive treatment outcome.

Tumor oxygenation during PDT has been measured with needle electrodes but the intratumoral distribution of this oxygen is not known. Irradiation fractionation with dark intervals on the order of a couple of minutes has been shown to induce three times more necrosis than continuous therapeutic irradiation, an effect that has been explained by tissue re-oxygenation during the dark periods. Finally, since the sensitizer photobleaches via singlet oxygen mediated processes, its fluorescence level can be regarded as an indicator of tissue oxygenation.

Measurements of Parameters Related to PDT

Some examples are given below, describing measurement methods which may be used for direct or indirect measurement of different parameters of PDT. The measured parameters provide for determination of a status of target tissue during PDT treatment, and may be useful as input data in a calculation method for monitoring and adjusting treatment parameters during photodynamic light therapy. The measurement methods are not limited to those, which are described herein. Any other suitable measurement method, which may be appropriate for providing a parameter useful as input data in embodiments of the calculation method of the invention may be implemented.

Oxygenation and Blood Flow

Any suitable technique for oxygen luminescence may be used to determine local oxygen concentration in photodynamic therapy.

Near-infrared diffuse reflection spectroscopy and diffuse correlation spectroscopy (DCS) may be used to simultaneously measure the concentration, oxygenation, and flow characteristics of blood cells.

Laser Doppler flowmetry and laser Doppler imaging is a method for non-invasive and continuous assessment of blood flow. The techniques are based on the phenomenon that monochromatic light trans-illuminating a tissue is spectrally broadened owing to scattering by moving blood cells. The use of Laser Doppler measurements in PDT is described in more detail in PCT/SE2006/050121 of the same applicant as of the present application, which is incorporated by reference herein in its entirety.

Sensitizer Concentration

Any suitable technique for measuring sensitizer concentration in tissue may be used. The sensitizer concentration may be measured using a fluorescence spectroscopy technique. A preferred method is to use a set of optical fibers placed near the treatment site, as e.g. described in U.S. Pat. No. 7,037,325 of the same proprietor as the applicant of the present application, which is incorporated by reference herein in its entirety.

Fluence Rate Distribution

Any suitable optical method may be used. A preferred method is to use a set of optical fibers placed near the treatment site, such as disclosed in U.S. Pat. No. 7,037,325.

Temperature

Any suitable optical method may be used to determine tissue temperature in photodynamic therapy, wherein the photodynamic therapy may be combined with photothermal therapy. Temperature of the tissue to be treated may for instance be monitored by the same fibers of the PDT system used for therapy, as e.g. described in U.S. Pat. No. 7,037,325.

According to an embodiment of the invention, a calculation method for monitoring and adjusting treatment parameters during photodynamic light therapy is provided. A light dose distribution from measured PDT parameters is obtained and a correction of light delivery conditions from said parameters may be used to control PDT treatment.

System and Apparatus

A system that may be useful for implementing embodiments of the present invention is for instance described in Swedish patent SE 503408 of the same proprietor as the applicant of the present application, which is incorporated by reference herein in its entirety.

Another PDT system suitable for implementing embodiments of the present invention is disclosed in WO04100789 of the same applicant as the applicant of the present application, which hereby is incorporated by reference herein in its entirety. WO04100789 discloses a PDT system using optical switches.

Yet another PDT system at least partly suitable for implementing embodiments of the present invention is disclosed in WO04101069 of the same applicant as the applicant of the present application, which hereby is incorporated by reference herein in its entirety. WO04101069 discloses a PDT system using translatory switches.

A further PDT system suitable for implementing embodiments of the present invention is disclosed in WO04100761 of the same applicant as the applicant of the present application, which hereby is incorporated by reference herein in its entirety. WO04100761 discloses a PDT system using purely mechanical and purely non-mechanical switching solutions in a synergetic way.

Another PDT system at least partly suitable for implementing embodiments of the present invention is disclosed in WO03041575 of the same applicant as the applicant of the present application, which hereby is incorporated by reference herein in its entirety. WO03041575 discloses a PDT system using rotating switches.

The above mentioned PDT system disclosed in EP 1470837 of Tulip, which hereby is incorporated by reference herein in its entirety, is also suitable for implementing embodiments of the present invention.

A schematically illustrated setup of an interstitial photodynamic therapy apparatus is shown in FIG. 1. The apparatus 100 allows for therapeutic light delivery and treatment monitoring via optical fibers 105. While in treatment mode, light from the therapeutic light unit 102 is guided into the distribution module 104 and directed into the patient fibers. Intermittently, the therapeutic irradiation is interrupted in order to perform measurement sequences, during which light from each of the diagnostic light sources is successively coupled into each of the optical fibers. The term "diagnostic" is here used to describe the status of the progression of the treatment and does not refer to diagnosis of the patient's status.

Utilizing the diagnostic light source, measurements related to PDT parameters, such as fluence rate distribution, sensitizer concentration and distribution, and tissue blood content and oxygenation are monitored. Examples for suitable measurement methods are for instance those describe above.

In some embodiments of the apparatus and method, the measurement sequences may be performed prior to commencing therapeutic light delivery and at varying time intervals during the entire treatment and thereby give information on the temporal profile of the PDT parameters, such as the fluence rate, the sensitizer level and the tissue oxygenation. In some embodiments of the apparatus these measurements of PDT parameters may also be performed in realtime, simultaneously with the therapeutic light delivery to the extent that such PDT parameter measurements are feasible without the therapeutic light interfering with the diagnostic measurements of the PDT parameters.

Thus, PDT may be controlled until a desired total light dose is delivered in a controlled and geometrically distributed way to the tissue to be treated, by means of what is described herein with reference to certain embodiments having substantial real time control.

In addition, to substantial realtime control of PDT, an overall PDT treatment session may be controlled in a manner as explained below with reference to FIGS. 14 to 16. Here, a PDT session may be interrupted and resumed, restricted or aborted in dependence of certain attributes, such as thresholds of photodynamic treatment parameters. For instance, when tissue oxygenation drops below a level where activation of a photosensitizing agent is ineffective due to lack of oxygen in the tissue, PDT treatment is interrupted and resumed when a sufficient level of oxygen is again present in the tissue to be treated. This may also be done on a fiber to fiber basis, i.e. locally with respect to the overall tissue volume under current treatment.

Upon start of PDT treatment, PDT is started by illuminating target tissue in a controlled manner, as described below in substantial realtime.

Figure 14:
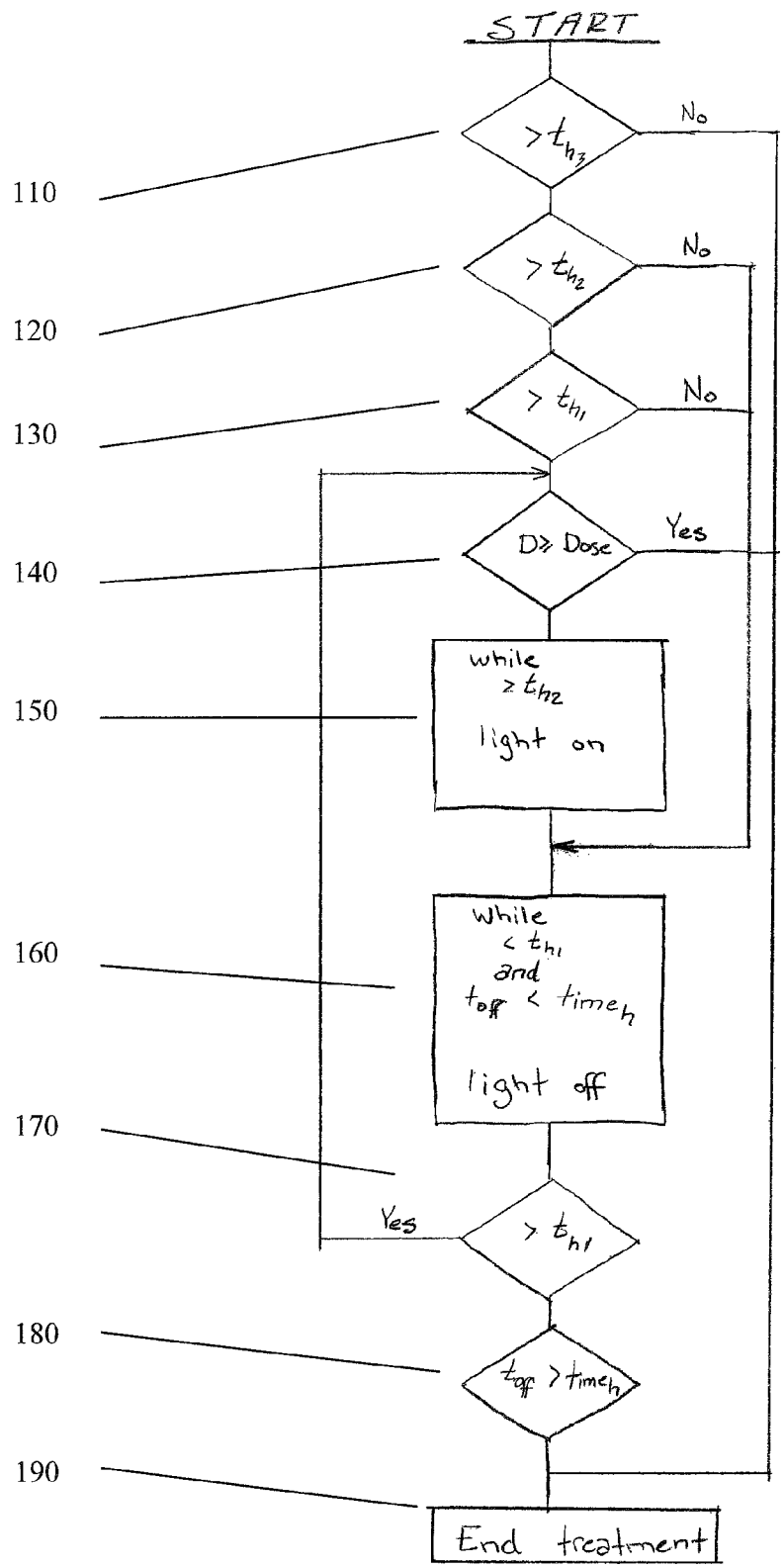
FIG. 14 is a flow chart illustrating an embodiment of a method of controlling PDT.

FIG. 14 is a flow chart illustrating an embodiment of a method of controlling PDT. A value of a photodynamic treatment parameter is taken as a basis for controlling delivery of PDT light, either to a total number of treatment fibers used, or a selection thereof, e.g. a single fiber or fibers in a specific sub region of the total tissue volume under PDT treatment in a PDT session. The value of the photodynamic treatment parameter may be an absolute value or a relative value, e.g. as a ratio of an initial absolute value at the beginning of the PDT therapy session.

A control device may be arranged as a regulator or a thresholding device in the PDT system to stop, or reduce or otherwise restrict said delivery of therapeutic light treatment at least temporary upon passing of at least one threshold value of the photodynamic treatment parameter. The at least one threshold value comprises in the present embodiment a first threshold $th_1$, a second threshold $th_2$, and a third threshold $th_3$, wherein the third threshold $th_3$ is lower than the second threshold $th_2$ and the second threshold $th_2$ is lower than the first threshold $th_1$. The first threshold $th_1$, the second threshold $th_2$, and the third threshold $th_3$ may be predetermined fixed values. Alternatively, the thresholds are dynamically adjustable during the interstitial PDT session. Also, the values may be fixed initially and the changed dynamically during the session. A dynamical adaptation of a threshold may comprise changing its value iteratively in dependence of the value of the photodynamic treatment parameter. For instance, if P is close to the third threshold, but lower than it, and this condition prevails for a certain defined time, the third threshold may be lowered, in order to resume delivery of therapeutic light.

Also, instead of shutting down light delivery, it may also be set to a maximum output operation during a final phase of treatment, e.g. near $t_e$.

In a first step 110, after start 110 of a PDT session, a comparison is made of the current value P of the photodynamic treatment parameter and a value of the third threshold $th_3$. In case P is below $th_3$, treatment is terminated as a continuation of the session will not improve treatment further. This may for instance be the case when all photosensitizer agent is used. In case P is above $th_3$, the method continues to a second step 120.

In the second step 120, a comparison is made of the current value P of the photodynamic treatment parameter with a value of the second threshold $th_2$. In case P is below $th_2$, the method continues at a step 160, where delivery of treatment light is switched off until P has reached a sufficient level above the first threshold $th_1$ or a timer stops treatment. In case P is above $th_2$, the method continues to a third step 130.

In the third step 130, a comparison is made of the current value P of the photodynamic treatment parameter with a value of the first threshold $th_1$. In case P is below $th_1$, the method continues at step 160. In case P is above $th_1$, the method continues PDT at a fourth step 140.

In the fourth step 140, a comparison is made of the delivered light dose D with a defined level thereof, such as determined by the Block-Cimmino algorithm. In case D is regarded sufficient, the PDT treatment session is terminated in step 190. In case more light dose has to be delivered to the tissue, delivery of therapeutic light is continued in step 150 while P is larger than the second threshold $th_2$. When P falls below the second threshold $th_2$, the method continues at step 160. Alternatively, the PDT session may be terminated by other criteria, e.g. a time limit or delivery of sufficient light dose.

Figure 15:
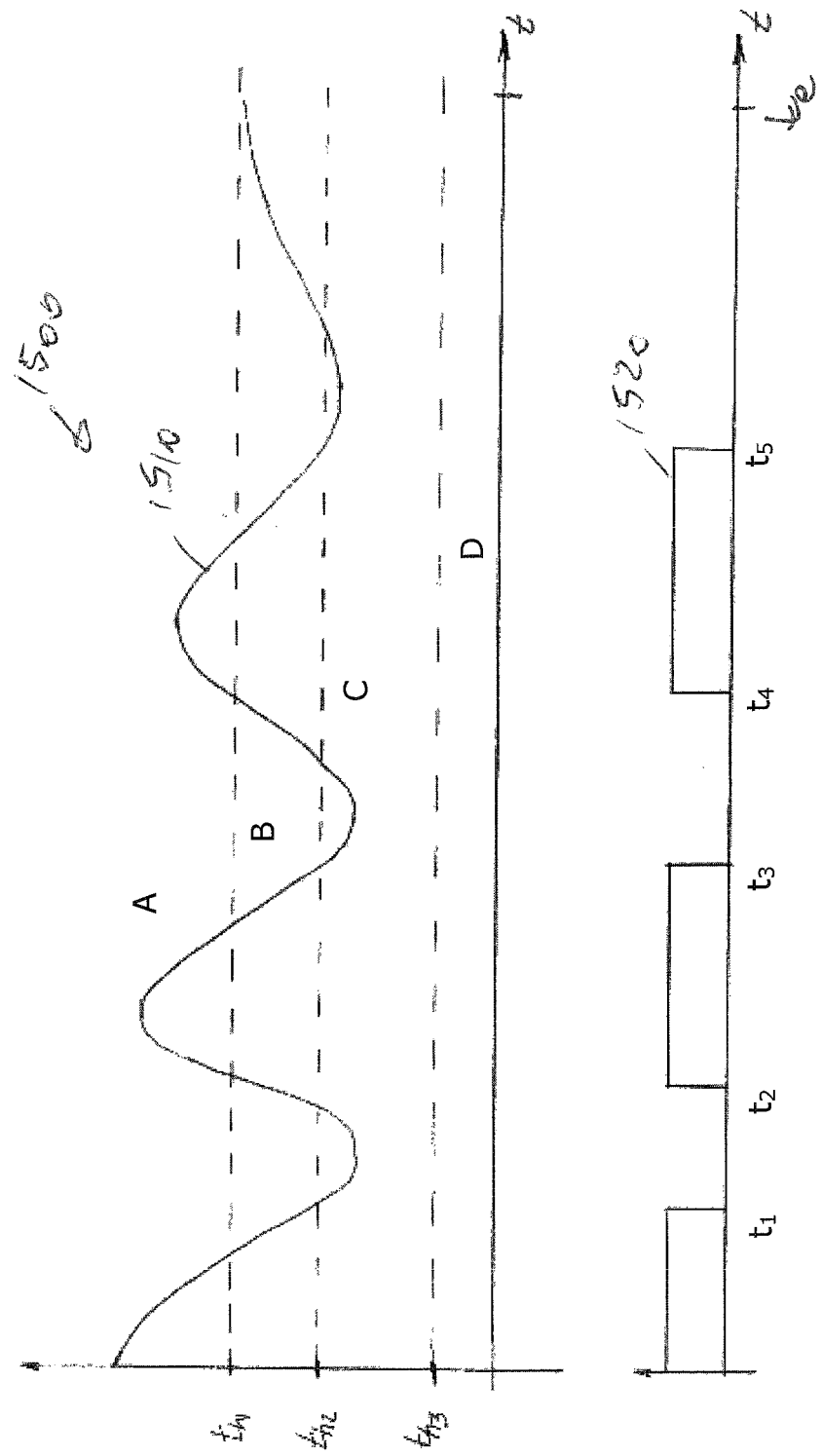
FIG. 15 is a timing diagram illustrating a practical application of the method illustrated in FIG. 14.
Figure 16:
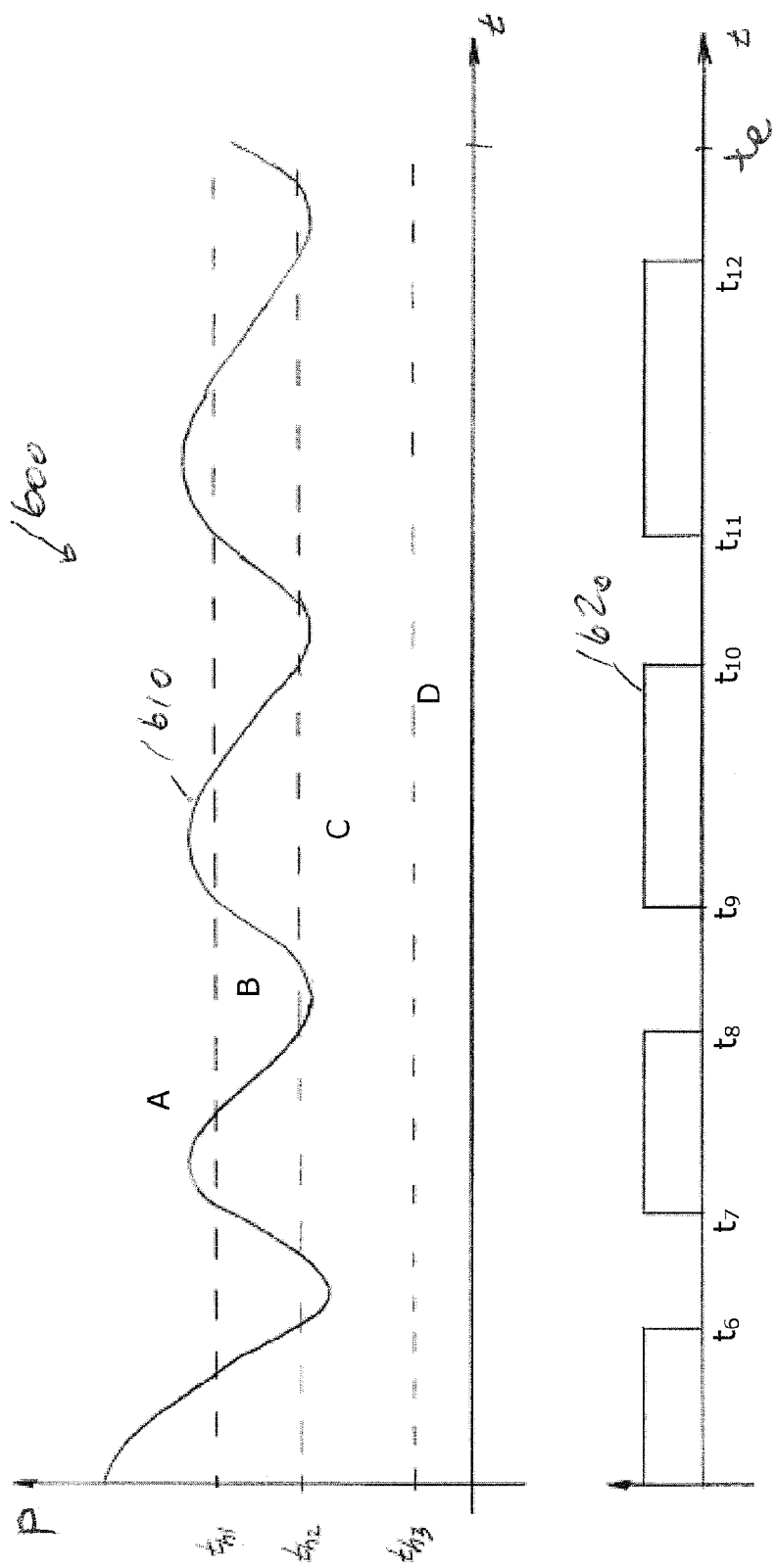
FIG. 16 is another timing diagram illustrating a practical application of the method illustrated in FIG. 14.

FIGS. 15 and 16 are timing diagrams 1500 and 1600 respectively illustrating practical applications of the method illustrated in FIG. 14. In the upper part of the graph, P is plotted over time, shown as a curve 1510 and 1610. In the lower part, a control signal for setting light delivery on or off, or restricting delivery, is illustrated. According to the above criteria, in FIG. 15, therapeutic light 1520 is switched off or restricted at times $t_1$, $t_3$, and $t_5$. Delivery of therapeutic light is resumed at times $t_2$, and $t_4$. At time $t_e$, the therapy session is terminated. Likewise, in FIG. 16 therapeutic light 1620 is switched off or restricted at times $t_6$, $t_8$, $t_{10}$, and $t_{12}$. Delivery of therapeutic light is resumed at times $t_7$, $t_9$, and $t_{11}$, wherein at time $t_e$, the therapy session is terminated.

Ranges of values P may be identified as A: normal treatment; B: prepare to stop or resume delivery; C: temporary stop treatment; and D: abort treatment session.

Alternatively, or in addition, to said thresholding device, a range identification device may be provided in embodiments of said PDT system for identifying and controlling an operational range of said system by means of said ranges A to D of values P.

Alternatively, or in addition, to said thresholding device, a derivative determining device may be provided, taking into consideration the gradient and direction of a curve of P for instance, when in range A and the curve has a negative gradient, i.e. declines towards range B, this might be an indication to maintain illumination at a high level or even increase light intensity to compensate for this effect. Another example is when P is in range B and the gradient is positive, i.e. the curve increases towards range A, initiation of resumed light delivery may be prepared in the PDT system.

The control device may be arranged to restrict the delivery of therapeutic light treatment at least temporary in dependence of at least one attribute of one of said photodynamic treatment parameters. Restriction maybe done by reducing output power of one or more a therapeutic light source, reducing illumination time, etc. The control device may be arranged to reduce the delivery of therapeutic light treatment at least temporary without stopping it completely. The control device may be arranged to stop the delivery of therapeutic light treatment at least temporary. The control device may be a regulator based on a difference between an actual value and a desired value of said photodynamic treatment parameter.

The photodynamic treatment parameter of the embodiment described above with reference to FIGS. 14 to 16 may be oxygenation of the tissue to be treated. Alternatively, or in addition, the control method may also be based on different photodynamic treatment parameters, such as blood flow in the tissue, light attenuation of said tissue, sensitizer concentration in said tissue, temperature in said tissue, etc.

In case several photodynamic treatment parameters control the overall PDT session, the criteria setting the delivery of treatment light to on or off is based on a first detected basis. That means one of said control loops base on a specific parameter gives a signal to put the therapy session on hold, this parameter is the one that may restart the therapy session again, independent of the other parameters. When the session is resumed, all control loops have equal preference again.

Figure 2:
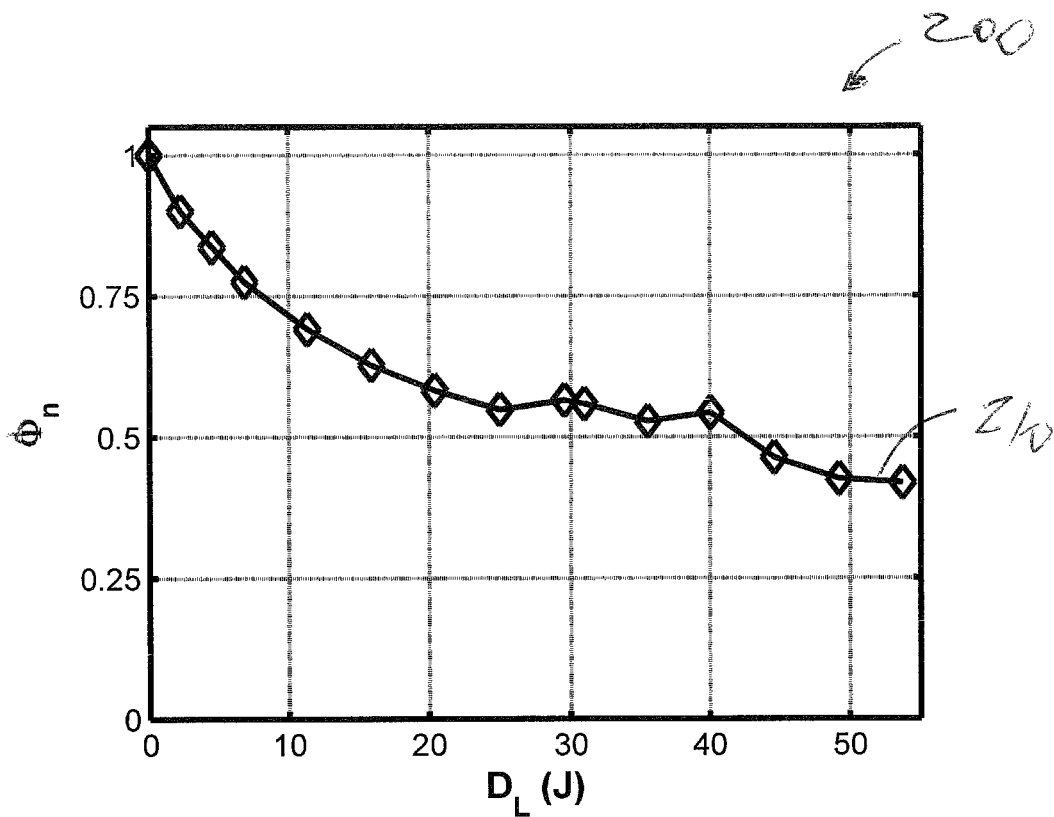
FIG. 2 is a graph showing a normalized light transmission between patient fibers as a function of the delivered energy. This measurement relates to the fluence rate distribution in the tissue.

An example of a measured temporal profile of the light transmission between patient fibers is shown in FIG. 2. The curve 210 is normalized to its initial value. The measurement was acquired with a source-detector separation of 7 mm. The fibers were placed in opposite quadrants of the target volume so that the detected light had probed the center of the lesion. The measurement illustrates the typical behavior of increased attenuation of the tissue as the light delivery progresses. Thus, this measurement relates to the fluence rate distribution in the tissue.

Figure 3:
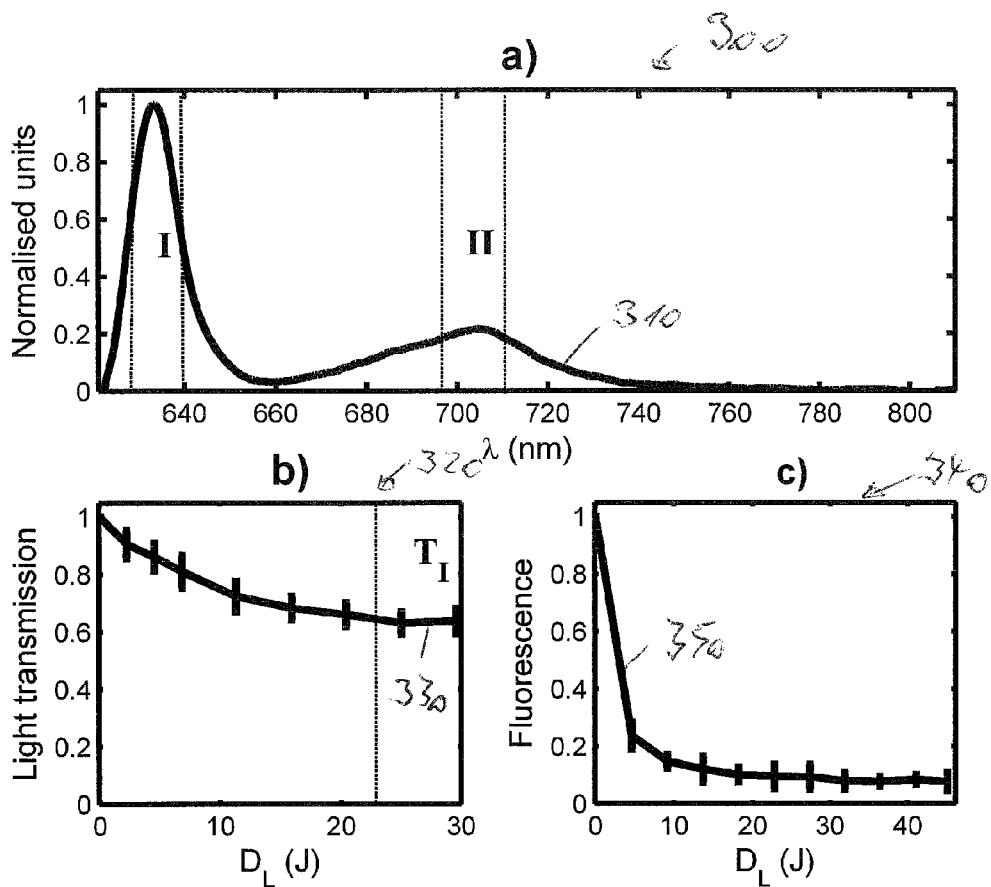
FIG. 3a is a graph showing raw spectrum from a diagnostic measurement using a 635-nm diode laser as a light source. Spectral intervals $\lambda_I$ and $\lambda_{II}$ indicate regions used for studying the light transmission at 635 nm and the photosensitizer fluorescence signals, respectively.
FIG. 3b is a graph showing an average of the normalized light transmission between neighboring patient fibers as a function of the delivered light dose ($D_L$) from one patient. Signals within area $T_f$ are averaged to constitute a measure of final light transmission.
FIG. 3c is a graph showing an average of the normalized PpIX fluorescence as measured between neighboring patient fibers as a function of the delivered light dose ($D_L$) from one patient, wherein in FIG. 3b and FIG. 3c error bars denote ±1 standard deviation.

An example of a typical spectrum 310 recorded when a diode laser emitting at 635 nm was used as the diagnostic light source is shown in FIG. 3a 300. Light transmission curves 330 as a function of delivered light dose are presented in FIG. 3b 320, similar to FIG. 2.

A photobleaching curve 350 for a typical sensitizer agent, namely protoporphyrin IX, is shown in FIG. 3c, where the average of the normalized fluorescence signal, as detected between neighboring patient fibers in one patient, is plotted as a function of the delivered light dose 340. Data from the treatments indicate rapid initial photobleaching, followed by a slowly decaying fluorescence level. It should be noted that other photosensitizers may exhibit other photobleaching characteristics, and the method according to certain embodiments of the invention is not limited to the described sensitizer, protoporphyrin IX.

Figure 4:
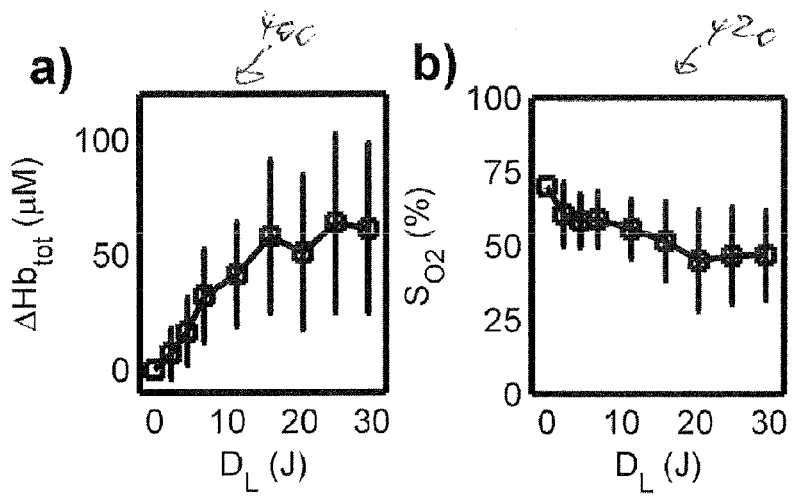
FIG. 4a is a graph showing an average change in total hemoglobin content.
FIG. 4b is a graph showing an average change in tissue oxygen saturation level.

FIG. 4 shows the change in average tissue blood volume 400 and oxygenation status 420 evaluated by spectral analysis of the absorption properties of oxygen-saturated and non-oxygen-saturated hemoglobin in the near-infrared wavelength region. Referring to FIG. 4a graph 400, it can be seen that the blood volume increases during the treatment, while the oxygen saturation decreases when referring to FIG. 4b graph 420.

Method to Determine Treatment Parameters

An aim of determining the PDT treatment parameters is to ascertain that a certain, pre-determined, light dose is delivered to each point in the tumor. The tissue status changes during the PDT treatment, as shown above. Therefore the fluence rate distribution will also change in each point of the PDT target tissue, the tumor. To ascertain that the target dose is reached, it is therefore necessary to adjust PDT treatment parameters. In embodiments this is done either by adjusting the emitted light power or the total time of light emission, or both.

In the following description of an embodiment of a method of calculation, the treatment parameter to be adjusted is the time of therapeutic light emission, but the same principle applies to adjusting the therapeutic light power. This is owing to the fact that the light dose is generally defined by the light power multiplied by the light emission time.

Figure 5:
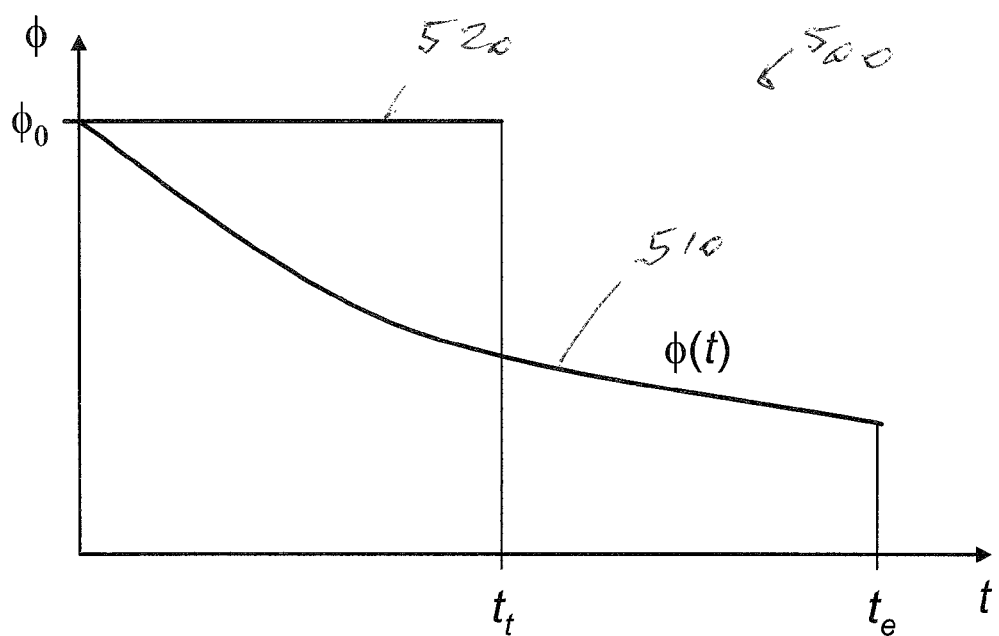
FIG. 5 is a graph showing a temporal progress of a fluence rate during a PDT treatment, wherein a rectangle bounded by $\Phi_0$ and $t_t$ represents the initial dose plan to reach the target dose $D_t = \Phi_0 t_t$. During the PDT treatment, the fluence rate decreases and in order to reach the target dose the light emission time needs to be extended to time $t_e$ so that the area under the curve is the same as the area of the rectangle.

FIG. 5 shows an example of a dose plan for one point in the tissue starting from an initial fluence rate $\varnothing_0$. The target dose for treatment of the target tissue is $D_t$. In order to reach $D_t$ a light emission time of $t_t$ is needed, so that $Dt=\varnothing_0 t_t$. This represents the area under the rectangular region 520 in the graph 500 shown in FIG. 5. In this example the fluence rate 510 decreases during the PDT treatment, e.g. due to the reasons given above, so that when the treatment time $t_t$ has been reached only the dose $$D = \int_0^{t_t} \phi(t)dt$$

has been delivered to the point in the tissue. Hence, the target tissue has been treated with a lower dose than $D_t$ as initially targeted. The treatment time therefore has to be extended to an extended treatment time $t_e$ so that the total dose is equal to $D_t$, i.e., the area under the curve is the same as the area under the rectangle.

The total treatment time is updated for each new measurement of the fluence rate to account for the changes in fluence rate. In some embodiments of the calculation method, this is done in realtime, i.e. the fluence rate is measured during ongoing therapy. The therapeutic light parameters are adjusted in a feedback loop based on the measured PDT treatment parameters.

The fluence rate may for instance be determined or estimated from the measurements by any of the methods described above, or in addition or alternatively by similar or equivalent measurement methods.

In an example, a method is used where the decay of the transmitted light at increasing distances in the tissue is recorded and fitted to a model for light propagation. A model that may be used is the transport equation for radiative transfer, as described in A. J. Welch and M. J. C. van Gemert: Optical-Thermal Response of Laser-Irradiated Tissue (Plenum Press 1995); and more specifically, an approximation based on the assumption of diffuse light propagation—the diffusion equation. The resulting data is the effective attenuation coefficient of the tissue, $\mu_{\mathit{eff}}$ evaluated using the equation $$-\ln(\phi_i r_i) = -\ln\left(\frac{P\mu_{\mathit{eff}}^2}{4\pi\mu_a r_i}\right),$$

wherein the index i denotes a measurement from a detector fiber i, and $r_i$ is the distance from the light source to each detector fiber, wherein i is an integer larger or equal to one, denoting the number of fibers used in the PDT system, such as six, twelve, eighteen, or more fibers. Moreover, P denotes the light output power of the therapeutic light source used for fiber I and $\mu_a$ is the absorption coefficient. By using $\mu_{\mathit{eff}}$ and the diffusion equation, the fluence rate may thus be calculated in the tissue.

According to a more complex description, the model for the target dose may be described as a function of not only fluence rate but also other PDT treatment parameters, such as sensitizer concentration, and/or oxygen concentration, and/or blood flow.

Since oxygen is consumed in the photodynamic process it is of interest for the treatment efficacy to emit light only when oxygen is present at concentrations high enough to cause efficient treatment. The light emission may therefore be interrupted for time intervals to allow the tissue to replenish its oxygen supply. Accordingly, based on the measurements of oxygen concentration and distribution, if the tissue oxygen saturation falls below a first predetermined threshold, for instance approximately 40%, the therapeutic light emission is interrupted. If the oxygen saturation is above a second predetermined threshold, for instance approximately 50%, the therapeutic light emission will resume. In this manner, a more efficient treatment is provided, taking into consideration to provide a control for optimally exploiting the available sensitizer agent by providing a treatment environment with sufficient oxygen.

Availability of sensitizer agent in the tissue is a prerequisite for the photodynamic effect and success of a PDT treatment. The sensitizer agent will bleach away during treatment. In a control method of PDT treatment, therapy will be terminated when only a predetermined low amount of sensitizer agent is left in the target tissue. This termination is done by terminating the emission of therapeutic light. Also, an indication may be given to the operator to replenish the reservoir of sensitizer agent in the tumor, and PDT treatment may be resumed.

In an embodiment of this adjustment of treatment parameters, the PDT treatment is interrupted or stopped if the measured estimated sensitizer concentration falls below a predetermined termination threshold, for instance below 10% of the initial level, and the therapeutic light emission is terminated.

In order to take into account the light dose in all points in the tissue according to the methods described above, a method for simultaneous determination of treatment parameters for many points simultaneously is provided. The method also allows determination of treatment parameters for many light sources simultaneously. A complication when determining the treatment parameters for all tumor points is that healthy tissue which surrounds the tumor should be spared from too high light dose. Another issue is thus to determine the correct light delivery times (or light power) in order to reach a sufficient light dose in the tumor while minimizing the dose to the surrounding tissue.

As before, light emission times are used as treatment parameters in the control method, but the same principle applies to light power. The stated problem is an inverse problem in that the desired outcome (light dose) is known and the light emission times that are necessary to reach this outcome are sought.

In a discrete description the dose in each point, indexed j, in the tissue may be written as $$D_j = \langle a^j, t \rangle,$$

where $$\langle a^j, t \rangle = \sum_{i=1}^{I} a_i^j t_i,$$

wherein $a_i^j$ represents the fluence rate in point j due to source i, $t_i$ the light emission time of source i, and there are i light sources, wherein i is an integer equal to or larger than one.

The aim is to reach a sufficient light dose $D_t^j$ in each point of the target tumor tissue and to avoid reaching a too high light dose $D_s^j$ in each point in the healthy tissue surrounding the target tumor tissue. This requirement is written as $$\langle a^j, t \rangle \geq D_t^j \; j=1,2,\ldots,J,$$

$$\langle a^j, t \rangle \leq D_s^j$$

wherein J is the total number of discrete points. The threshold doses $D_t^j$ and $D_s^j$ may be individually defined or defined for blocks of points in the tissue. A system of inequalities results, which may be solved mathematically by a method for solution of such systems.

In the present embodiment a variation of Cimmino's method is used to solve the system of inequalities, based on block action. Cimmino's method is described in Y. Censor et. al.: "On the use of Cimmino's simultaneous projections method for computing a solution of the inverse problem in radiation therapy treatment planning", Inverse Problems 4, 607 (1988), which is incorporated by reference herein in its entirety.

The blocks refer to blocks of points in the tissue sharing the same threshold dose values. Cimmino's method is an iterative algorithm where the current estimate is projected onto each half-space bounded by the hyperplane represented by each inequality. Once sufficient convergence has been reached, Cimmino's method gives a solution that is the light emission times that are close to the optimal for giving the desired light dose in each point.

The described embodiments of the present invention disclose a method wherein the treatment parameters for all light sources are determined by taking all points in the relevant tissue volume into account. The determination of treatment parameters may be performed prior to commencing therapeutic light emission and then repeated after each measurement sequence to provide updated treatment parameters that reflect the changes in tissue status that has occurred as a result of the treatment or other physiological processes.

DEFINITIONS

PDT Photodynamic Therapy
$\Phi$ Fluence rate (W/m$^2$)
$D_t$ Target dose (J/m$^2$)
$D_s$ Threshold dose to surrounding healthy tissue (J/m$^2$)
t Time (s)
$a_i^j$ Fluence rate in point j due to light source i
i Index to light sources
j Index to discrete points in tissue
I The total number of light sources
J The total number of discrete tissue points
$\mu_{eff}$ The effective attenuation coefficient (1/m)
$\mu_a$ Absorption coefficient (1/m)

More specific examples of embodiments with reference to prostate treatment will be given below.

The following embodiments of the invention relate to a treatment of prostate cancer using Interstitial Photodynamic Therapy (IPDT) with realtime treatment dosimetry.

Interstitial PDT (IPDT) is regarded an alternative to radical prostatectomy, external radiation and chemotherapy for the treatment of localized prostate cancer. For example, the photosensitizer agent Temoporfin (mTHPC, meso-tetra(hydroxyphenyl)chlorin) is used for treating secondary and primary prostate cancer. Utilizing bare-ended fibers, the delivered light doses were 20 to 100 J per treatment site, resulting in significant treatment induced necrosis and decreasing prostate-specific antigen (PSA) levels. Four of six primary cases experienced only very minor complications, including transitory irritative voiding symptoms, whereas the more serious complications included stress incontinence and one case of deteriorated sexual function. For the secondary cases, PSA eventually started to increase again and tumor recurrences in 13 out of 14 patients required antiandrogen therapy post PDT. According to the authors, a more detailed drug and light dosimetry might lead to better discrimination between target tissue and surrounding sensitive organs.

IPDT has been performed for recurrent prostate cancer using the vascular-targeted photosensitizer agent Tookad (WST09). During phase I clinical trials both light (100 to 360 J/cm) and drug ($\leq 2$ mg/kg) dose-escalation studies were carried out. At the maximum drug dose, lesion formation was observed to primarily depend on the total light dose. Furthermore, Hahn et. al.: "Preliminary results of interstitial motexafin lutetium-mediated PDT for prostate cancer," Lasers Surg. Med. 38(5), 427-434 (2006), have utilized the photosensitizer agent motexafin lutetium for the treatment of recurrent prostate carcinoma in combination with monitoring light fluence, drug level and oxygen distribution. However, these parameters were only monitored and no indication is given how these parameters may be used to control IPDT itself.

The photosensitizer agent Aminolevulinic acid (ALA)-PDT has been investigated, resulting in decreasing PSA levels and no evidence of incontinence or dysuria after PDT. Among many others, the cited references indicate that IPDT is a relatively safe treatment modality capable of inducing significant tissue necrosis within the prostate.

PDT preserves structural connective tissue, such as collagen, and has been shown to maintain the integrity of the prostate gland. Ideally, by careful light dosimetry one might target the entire prostate while sparing sensitive surrounding organs to minimize recurrences and treatment-related complications. However, giving initial evidence for the complexities associated with prostate PDT dosimetry, many PDT-trials on prostate tissue report on large intra and inter-patient variations in treatment-induced necrotic volumes despite delivering similar drug and light doses. These effects might partly be explained by inter- and intra-patient variations of the light absorption and scattering coefficients, directly influencing the light distribution within the prostate tissue. In addition, any treatment-induced variations in tissue composition, such as changing blood volume and tissue oxygenation status, also affect the light levels within the target tissue.

Hence, there is a need for more accurate and individualized realtime dosimetry, both for PDT on prostate tissue and in more general terms. There are numerous reports on prostate in vivo spectroscopic measurements of parameters related to the PDT effect, e.g. light fluence rate, sensitizer distribution, and tissue oxygenation as well as blood flow and volume. Such studies hold great potential in increasing the understanding of the processes associated with PDT on prostate tissue and in extending clinical prostate-PDT to also incorporate individualized treatment dosimetry and realtime treatment feedback.

Algorithms constituting a realtime dosimetry module for IPDT on prostate tissue with treatment feedback based on a light dose threshold model are described. The prerequisite is the development of an instrument with a maximum of 18 thin optical fibers that can be utilized for therapeutic light delivery as well as monitoring of tissue optical properties, sensitizer concentration and tissue oxygen saturation during the course of the treatment.

As mentioned above, an apparatus for IPDT is provided that incorporates realtime monitoring of the light transmission signals between the treatment fibers in order to evaluate the light effective attenuation coefficient. These data together with information on the tissue geometry are used as input for a Block-Cimmino optimization algorithm, predicting individual fiber irradiation times. By iterating measurements, calculation of the light effective attenuation and the Block-Cimmino optimization procedure, the irradiation times for each source fiber may thus be continuously updated throughout the treatment session.

The finite element method (FEM) is utilized to simulate light transmission signals within a realistic prostate model for temporally and spatially varying tissue optical properties. Based on the simulated data set, the ability of the algorithm is verified to be capable of tracking an increase in the effective attenuation coefficient within the prostate gland. Furthermore, via tissue importance weighting within the Block-Cimmino algorithm the possibilities to discriminate between target tissue and organs at risk (OAR) in terms of the deposited light dose is evaluated. Finally, the dose volume histograms (DVHs) of the light dose delivered during an IPDT treatment with a simulated absorption increase are compared with and without treatment feedback. In this way, the feasibility is determined for an IPDT dosimetry model that ascertains a certain predetermined light dose within the target tissue irrespective of any treatment-induced changes in tissue absorption.

Methods and Algorithms

Providing an introduction to our realtime dosimetry software, Section A gives a brief overview of the clinical treatment procedure as well as a few technical details related to the IPDT instrumentation. Sections B, C, D and E separately describe the procedures and software modules used for, in order, creating the 3D geometry, calculating the fiber positions within the prostate, evaluating the light effective attenuation coefficient, and, finally, calculating the individual fiber irradiation times. The combination of these software modules constitute what is referred to as the realtime dosimetry module. Section F describes the use of the FEM to simulate the light distribution within a realistic prostate geometry, thus providing realistic test data for the algorithms constituting the realtime dosimetry module.

A. Treatment Procedure

Figure 6:
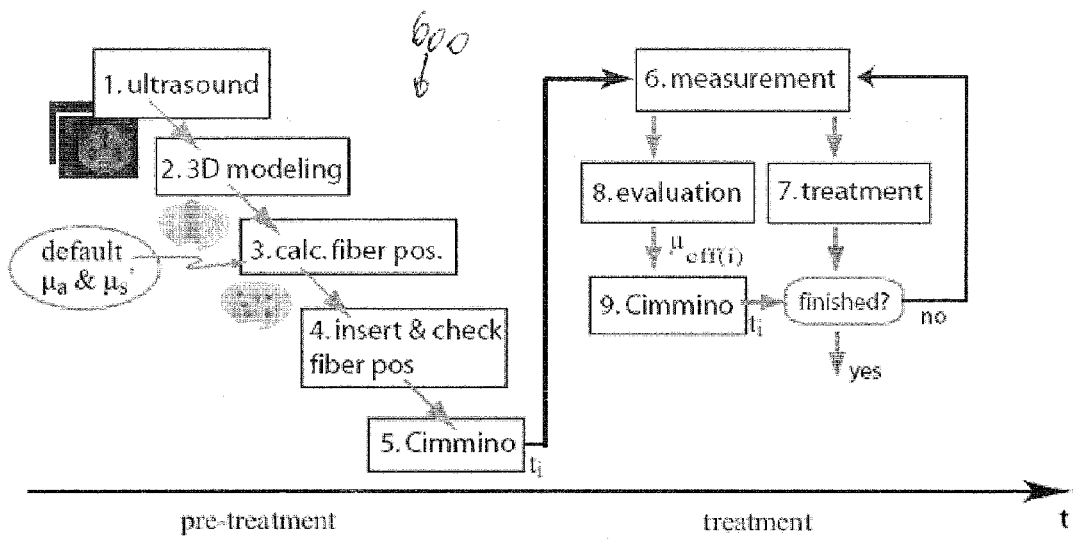
FIG. 6 is a flow chart illustrating the pre-treatment planning as well as the treatment and monitoring sequences that constitute the realtime dosimetry module.

The IPDT treatment 600 as outlined in FIG. 6 comprises dosimetry software has been developed to execute on the aforementioned IPDT apparatus that utilizes a maximum of 18 optical patient fibers. The patient fibers may for instance be bare-ended 400-µm diameter optical fibers for delivery of therapeutic light. The therapeutic light may be around 652 nm, matching one of the absorption bands of the photosensitizer Temoporfin. By means of internal optical units, the instrument may switch between treatment mode, during which all fibers emit therapeutic irradiation, to diagnostic measurement mode, wherein one fiber at the time is active and six neighboring fibers detect the transmitted light. The detection unit consists of six spectrometers covering the spectral interval between 630 and 840 nm.

The treatment session consists of pre-treatment and treatment procedures where a graphical user interface guides the urologist through the treatment procedure.

At first, an ultrasound investigation of the prostate is performed to assess the geometry of the target tissue as well as nearby OAR, step (1). Within a set of 6 to 10 ultrasound images, the urologist may delineate the extent of the prostatic gland, urethra, rectum, upper and lower sphincters and the cavernous nerve bundles. The tissue contours are then patched into a three-dimensional voxel representation of the geometry containing all organs, step (2). As the patient is prepared for surgery, a random search algorithm calculates the near-optimal source fiber positions within the reconstructed geometry, step (3).

Figure 7:
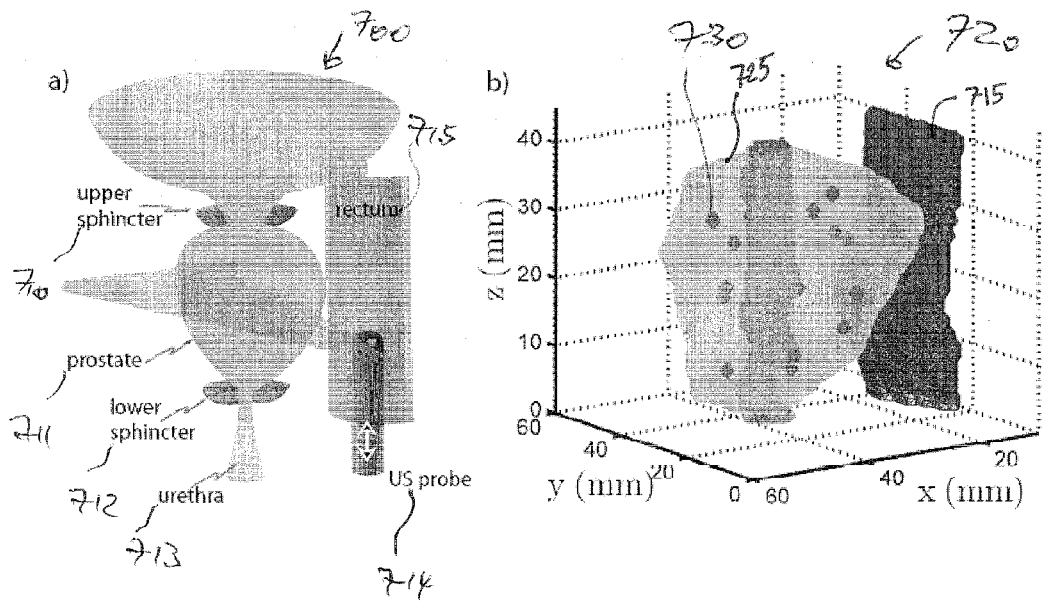
FIG. 7a is a schematic drawing of organs incorporated into a prostate dosimetry model.
FIG. 7b is a three dimensional graph that shows the reconstructed geometry of a patient target site.

FIG. 7 illustrates a sample three-dimensional geometry model 720, with 1 mm voxel side lengths, including the target tissue 725, i.e. the prostate 711, the OAR, consisting of the urethra 713, rectum 715, and normal, surrounding tissue as well as the source fiber positions 730. This geometry, representing the "test" geometry used in this work, was created based on eight ultrasound images from a patient with a glandular volume of approximately 27 cm3 and treatment fiber positions were calculated by the algorithm described in Section C.

Utilizing hollow steel needles, the optical fibers, also referred to as treatment fibers, are guided into position, step (4). Within this fourth step, the urologist is given the opportunity to update the final fiber positions as these might deviate slightly from the set of positions calculated by the random-search optimization algorithm. Information on the geometry and the actual fiber positions is used as input for the Block-Cimmino optimization algorithm to predict required irradiation times for all source fibers, step (5).

Following the pre-treatment planning, the IPDT session involves iterating measurement, step (6), and treatment, step (7), sequences. Measurements are performed prior to as well as at varying time intervals after the start of therapeutic light delivery. Immediately following a measurement sequence, delivery of therapeutic irradiation, step (7), runs in parallel to evaluating the measurement data to assess the effective attenuation coefficient within volumetric subsets of the prostate gland, step (8). The Block-Cimmino algorithm, step (9), is then executed in order to update the fiber irradiation times. Steps (6) to (9) are iterated until the remaining treatment time as predicted by the Block-Cimmino algorithm equals zero. The implemented scheme, where steps (8) and (9) constitute the realtime dosimetry module, is also referred to as Interactive Dosimetry by Sequential Evaluation (IDOSE).

B. Geometry Model

The geometry model is a three-dimensional voxel representation of the target organ, here the prostate, and the adjacent urethra, rectum, upper and lower sphincters and the cavernous nerve bundles, as risk organs. When manually or semi-automatically determining the organ positions in the 3D patient data set, the physician for instance marks five to twenty points, within six to ten ultrasound images, delineating the periphery of the different tissue types present in that particular cross-section. These points are then connected by linear interpolation to form connected organ contours. From the ultrasound investigation, the transversal images are craniocaudally separated by five mm.

The tissue contours may be linearly interpolated to regions in between ultrasound cross-sections, giving voxel side lengths of 1 mm in all three dimensions. A filling technique is applied to specify the tissue type for voxels within the delineated contours; first every voxel within the three-dimensional matrix is initiated to normal tissue except for voxels containing the contours of any other tissue type. Then, the center of each set of contour points is calculated. For each tissue type, the following procedure is executed; first, the center point of the current tissue type is put in a buffer. The first point in the buffer is then extracted and set to the same tissue type as the current tissue type. Thereafter its six connected neighbors are tested for tissue type. If a point does not belong to the same tissue type as the current contour point and does not belong to another set of contour points it is put into the buffer. This procedure is repeated until the buffer is empty, thus filling every tissue type from its center and outwards. The reconstructed voxel model has typical side lengths of 60-65 voxels.

TABLE 1

Tissue specific weights ($\omega_j$) used for optimizing fiber positions, fluence range (lower value $L_j$ and upper value $U_j$) and weights ($\alpha_j$) used for the Cimmino optimization algorithm.

| Tissue type | $\omega_j$ | $L_j$, $U_j$(J/cm²) | |
|---|---|---|---|
| Normal tissue | 0 | 0-5 | 1e-4 |
| Upper sphincter | −1 | 0-5 | 0.1 |
| Lower sphincter | −1 | 0-5 | 0.2 |
| Rectum | −1.7 | 0-5 | 0.1 |
| Prostate | 1 | 5-Inf | 2 |
| Urethra | −0.85 | 0-5 | 0.1 |

C. Fiber Positions

The task of finding the optimal fiber positions may be formulated as maximizing the light fluence rate within the target organ, here the prostatic gland, while minimizing the light distribution within the organs at risk (OAR) adjacent the target organ to be treated. The optimization algorithm is an iterative random-search algorithm similar to a simulated annealing type algorithm. The search for optimal fiber positions is initialized by creating a random configuration of source positions within the prostate. The bare-ended fibers are modeled as isotropic point sources where the fluence rate in voxel j due to a source in voxel i, $\phi_{ij}$, is approximated by the analytical solution to the diffusion equation within an infinite, homogeneous medium:

$$\phi_{ij} = \frac{P\mu_{eff}^2}{4\pi\mu_a r_{ij}} \exp(-\mu_{eff} r_{ij}), \qquad (1)$$

wherein P denotes the light source effect, set to 0.15 W in this example, and the effective attenuation coefficient is given by where $\mu_{eff}=[3\mu_a(\mu_a+\mu_s')]^{1/2}$, where $\mu_a$ and $\mu_s'$ were set to 0.5 and 9.7 cm$^{-1}$, respectively. For every iteration, each fiber is moved a limited length in a random direction.

The movement is restricted to voxels within the prostate and only one source fiber per voxel is allowed. Following a fiber movement, a fitness value is computed to evaluate the quality of the configuration:

$$F = \sum_{j=1}^{M} \omega_j^{target} \phi_{ij} + \sum_{j=1}^{N} \omega_j^{OAR} \phi_{ij} \qquad (2)$$

The first summation in equation (2) includes 25% of the prostate voxels with the lowest fluence rate. The target target tissue weights, $W_{ij}^{target}$, are positive, contributing constructively to the fitness value when delivering light to this particular region. Correspondingly, the second summation in formula (2) includes 25% of the voxels within OAR, i.e. the urethra, rectum, upper and lower sphincters and the cavernous nerve bundles, characterized by the highest fluence rate. The corresponding tissue weights are given in Table 1 above, where each $w_{ij}^{OAR}<0$, thereby causing any fluence rate within organs at risk to punish the overall fitness function value. Equation (2) thus seeks to maximize the lowest fluence rate values in the prostate while minimizing the highest fluence rate values outside the target tissue.

For the iterative scheme, the new fiber positions are accepted only if a fiber movement leads to a higher fitness function value. As the light distribution may be considered diffuse at the earliest a distance $1/\mu_s'$ from the fiber tip, the resulting fiber positions are presented with the depth coordinate decreased by this distance.

Random-search algorithms of this type are not guaranteed to find the global optimum. However, the stochastic movements increase the probability that the search may find its way out of a local optimum. In the current implementation the maximum step size is decreased gradually from three to one voxel to ensure that the solution will converge to an optimum, although this is at the expense of the ability to circumvent local optima. Typical execution times were on the order of 45 to 60 minutes, but may be minimized by alternative or future calculation hardware improvements.

D. Optical Properties

As the measurement sequences are executed during the therapeutic session it is of ample importance that the scheme used to evaluate the tissue optical properties from the light transmission signals is fast and requires limited computational cost. All measurements are performed in steady-state with source-detector separations on the order of 10 to 25 mm and diffuse light propagation is assumed. Hence there is no possibility to separate the absorption and scattering coefficients. Instead, the evaluation scheme aims to quantify the effective attenuation coefficient, $\mu_{eff}$, given that the reduced scattering coefficient remains fixed throughout the prostate volume. During a measurement sequence, the light transmission signals between each individual source fiber and its six neighboring fibers are monitored. By limiting the number of detection fibers to six, the probed tissue volume is restricted to regions close to the source fiber. The transmission signals are monitored sequentially for each source fiber, thus creating 18 localized but partially overlapping sub-geometries. Within each sub-geometry, the tissue is assumed homogeneous and characterized by a fiber-specific $\mu_{eff}$. Furthermore, by modeling the interstitially positioned source fibers as isotropic point sources, the Green solution to the diffusion equation may be used to describe the fluence rate:

$$\phi_{ij} = \frac{P\mu_{eff}^2}{4\pi\mu_a |r_j - r_i|} \exp(-\mu_{eff}|r_j - r_i|) \quad i = 1, 2, \ldots, 18 \quad (3)$$
$$j = 1, 2, \ldots, 6$$

Here, $\phi_{ij}$, denotes the fluence rate at a location $r_j$ due to a point source at $r_i$. Furthermore, P is the fiber output power and the effective attenuation coefficient is defined by $\mu_{eff} = \sqrt{3\mu_a(\mu_a + \mu_s')}$.

Both $\phi_{ij}$ and $\phi_{ji}$ are measured and hence twelve measurements may be used to assess a fiber-specific $\mu_{eff(i)}$ of fiber i. Ideally, the logarithm of the fluence rate multiplied with the source-detector separation, $|r_j - r_i|$, is a first order polynomial with respect to $|r_j - r_i|$ where the slope yields $\mu_{eff}$:

$$\ln(\phi_{ij}|r_j - r_i|) = \ln\left(\frac{P\mu_{eff(i)}^2}{4\pi\mu_a}\right) - \mu_{eff(i)}|r_j - r_i| \quad (4)$$

Here, the notation corresponds to that of Equation (3). The linear fit is performed for each source fiber, resulting in 18 different coefficients, $\mu_{eff(i)}$. The procedure may be regarded as discretizing the entire gland into 18 sub-geometries centered around the source fibers, where each sub-geometry is assumed to be homogeneous, infinitely large and characterized by a fiber-specific attenuation coefficient. The fiber positions may for instance be sorted so that a part of the fibers, e.g. fibers 1 to 9 are located within the left lateral lobe of the gland at increasing distance from the prostate apex. The remaining fibers, in the example fibers 10 to 18, may for instance be sorted in decreasing order from the apex but within the right lateral lobe. For each source fiber i the six neighbors used for light transmission measurements are i−3, . . . , i+3. In this way, probing light transmitted through the urethra is minimized. This protects the urethra from unwanted exposure to activation light, which in turn minimizes activation of photosensitizer agent in the urethra. Photosensitizer is often administered intravenously and thus transported with the blood flow and present in the entire body. Thus, the urethra is protected from unnecessary exposure to toxic singlet oxygen that otherwise was activated by the probing light. In similar ways other OAR may be spared from this toxic load by avoiding illumination thereof. In this manner efficacy of a PDT treatment is advantageously enhanced.

To reject non-valid measurements, only transmission signals with a sufficiently high signal-to-noise-ratio (SNR) are used for evaluating $\mu_{eff(i)}$. In the example, the SNR is defined as the light transmission summed between 648 and 656 nm divided by the standard deviation (SD) of detector dark noise. Also, the source-detector separations a required to span a sufficiently large distance to allow a robust linear fit and validity of Equation (4). In the current implementation, the algorithm used for evaluating $\mu_{eff(i)}$ thus requires specifying a SNR-threshold as well as a threshold for the standard deviation (SD) of $|r_j - r_i|$. If all transmission signals from a particular source fiber are characterized by sufficient SNR and range of source-detector separations, the linear fit is performed and the calculated effective attenuation coefficient is assigned to that source fiber. If the number of valid measurements is less than six, due to either noise rejection or too limited source-detector distances, the transmission signals from two source fibers are combined and incorporated into the linear fit. This effectively expands the volume of the analyzed sub-geometry. If the number of valid measurements within the expanded sub-geometry is still less than six, further addition of sub-geometries is performed. The maximum number of included sub-geometries is 18, for which case the whole tissue geometry is analyzed as one unit. In the data post-processing, the evaluated effective attenuation coefficients are checked to be within a pre-defined range, otherwise all $\mu_{eff(i)}$ are set to a default value. Table 2 lists specific parameters that are used within this software module.

TABLE 2

Input parameters for the module evaluating target tissue optical properties.

| Parameter | Value |
| --- | --- |
| SNR threshold | 3 |
| r-SD | 3 mm |
| $\mu_{eff}$-range | 1-8 cm$^{-1}$ |
| $\mu_{eff}$-default | 3.7 cm$^{-1}$ |

In other embodiments, other numbers of fibers and sub-geometries may be chosen than those of the present example.

E. Irradiation Times

The Cimmino optimization algorithm may be used for radiation therapy treatment planning and also for determination of light diffuser positions, lengths and strengths in prostate IPDT treatment planning. In the present embodiment, the Block-Cimmino optimization algorithm is employed for the inverse problem of finding individual irradiation times, $t_i$, for I isotropic point sources. The algorithm accepts information on the tissue optical properties and the tissue geometry to calculate irradiation times for each treatment fiber i. The optimization conditions may be expressed as the requirement to deliver a light dose exceeding a pre-determined threshold dose to the target tissue, i.e. in the embodiment the prostate glandular tissue, while minimizing the dose to the OAR, here defined as the urethra, rectum and normal, surrounding tissue. The optimization problem can thus be formulated as satisfying the following system of inequalities for the fluence,

TABLE 3

Input parameters for the Block-Cimmino optimization algorithm.

| Parameter | Prostate | Rectum | Urethra | Normal |
|---|---|---|---|---|
| Lj (J) | 5 | 0 | 0 | 0 |
| Uj (J) | ∞ | 5 | 5 | 5 |
| αj | 10 | 5[a] | 0.1 | 1e−8 |

[a] Varied between 1e−4 and 500.

i.e. the fluence rate, Ø, multiplied by the irradiation time, t, in all tissue voxels:

$$L_j \le \langle \phi_j, t \rangle = \sum_{i=1}^{I} \phi_{ij} t_i \le U_j \quad j = 1, 2, \ldots, J \quad (5)$$

$$t_i \ge 0 \quad\quad\quad i = 1, 2, \ldots, 18,$$

wherein J is the number of tissue voxels and $L_j$ and $U_j$ represent tissue type specific lower and upper threshold doses, respectively. Table 3 lists the thresholds used in this example. These threshold levels were found reasonable from the clinical work. $Ø_{ij}$ is given by Equation (3), where each source fiber is characterized by a specific $\mu_{eff(i)}$ as described in Section D. In the example, a fiber output power of 0.15 W is assumed for all fibers. In other embodiments, another fiber output may be chosen, or different output powers for the individual fibers. When calculating the fluence rate distribution, the absorption and reduced scattering coefficients are separated. Here, we set $\mu_s' = 8.7$ cm$^{-1}$ and determine $\mu_{a(i)}$ from $\mu_{eff(i)}$.

Due to the large number of tissue voxels included in the problem, most often no feasible solution exists to Equation (5). However, the Cimmino optimization algorithm converges to a close approximation of the least-intensity feasible solution. In the embodiment, the block-action scheme as outlined by Censor et al. is implemented, where each voxel is ascribed a block corresponding to its tissue type, differentiating between prostate, urethra, rectum and normal tissue. The algorithm is based on an iterative scheme, starting from an arbitrary point in I-dimensional space. Non-violated constraints do not affect the new solution, whereas voxels experiencing light doses outside the specified range bring the successive iteration closer to the optimal solution defined by Equation (5). This procedure is described mathematically in Equations (6) and 7).

$$\tilde{t}^{k+1} = t^k + \lambda_k \sum_{j \in B_s} \alpha_j s_j(t^k) \phi_{ij}$$

$$t^{k+1} = \begin{cases} \tilde{t}^{k+1} & \text{if } \tilde{t}^{k+1} \ge 0 \\ 0 & \text{if } \tilde{t}^{k+1} < 0 \end{cases} \quad (6)$$

where $$s_j(y) = \begin{cases} 0 & \text{if } L_j \le \langle \phi_j, y \rangle \le U_j \\ \dfrac{U_j - \langle \phi_j, y \rangle}{\|\phi_j\|^2} & \text{if } U_j < \langle \phi_j, y \rangle \\ -\dfrac{\langle \phi_j, y \rangle - L_j}{\|\phi_j\|^2} & \text{if } \langle \phi_j, y \rangle < L_j \end{cases} \quad (7)$$

The iterations are stopped either when the solution has converged or when a stipulated maximum number of iterations has been reached. $\lambda_k$ is a relaxation parameter that controls the speed of convergence. To improve initial convergence, $\lambda_k$ is for instance set to 20, but this parameter is successively decreased in case oscillations occur between iterations. Each tissue type, i.e. block $B_s$, is given a certain weight, $\alpha_j$, which reflects the punishment associated with delivering a light dose outside the allowed interval. The sum of these tissue weights is normalized. In order not to let normal tissue voxels far away from the prostate influence the iterates in Equation (6), only a certain number of the normal tissue voxels experiencing the highest light doses may be included. This number may be calculated as the number of voxels on the surface of a sphere with the same volume as the prostate gland. The explicit $\alpha_j$ values used in this example are given in Table 3.

The Block-Cimmino algorithm calculates the total irradiation times for individual fibers based on the specific $\mu_{eff(i)}$ used as input parameters. Except for the first time, the algorithm executes, the fraction of the entire treatment session already completed during the previous treatment sequence(s) is subtracted from the newly calculated irradiation times. The output thus constitutes the remaining irradiation times based on the current set of $\mu_{eff(i)}$. When all $\mu_{eff(i)}$ have changed by less than 10% compared to the previous measurement sequence, or, in the case of the first measurement sequence, relative to the pre-treatment plan, which utilizes the default value of $\mu_{eff}$ given in Table 2, the Block-Cimmino algorithm is not executed. Instead, remaining fiber irradiation times are updated by subtracting the duration of the previous treatment sequence.

Although the Cimmino algorithm does not allow for straightforward implementation of illustrating dose volume histogram (DVH) constraints, the resulting DVHs are used to check the light dose distribution. In general, DVHs provide information on the tissue fractional volume that receives a certain treatment dose. Here, the dose is defined as the fluence, see also Equation (5), where $t_i$ are calculated by the Block-Cimmino algorithm and $Ø_{ij}$ are modeled by means of the FEM within the geometry 720 shown in FIG. 7. These simulations are described in Section F. The importance weights, $\alpha_j$, may be empirically adjusted to reflect the sensitivity of the different OAR and to discriminate these organs from the target tissue. In this embodiment, the aim is to deliver a light dose exceeding a pre-defined threshold in 85% of the target tissue, whereas a maximum of 25% of the voxels representing the rectum 715 is allowed this light dose. No dose restrictions are imposed on normal tissue 725 and urethra 713.

F. Modeling the Light Distribution

To provide realistic input for the realtime dosimetry module, the FEM (Multiphysics 3.3 R°, Comsol A B, Stockholm, Sweden) may be used to model the fluence rate distribution, $Ø_{ij}$, within the geometry illustrated 720 in FIG. 7. The target and risk organs are surrounded by a tissue block, representing normal tissue. With a side-length of 60 mm, in the example, this block is sufficiently large for boundary effects not to influence the solution. The fluence rate is determined by solving the steady-state diffusion equation:

$$-\nabla \cdot (D \nabla \phi_{ij}) + \mu_a \phi_{ij} = S(r_i) \quad i=1,\ldots,18 \quad (8)$$

In the example, the diffusion coefficient, $D=[3(\mu_a+\mu_s')]^{-1}$ and the bare-ended fibers 730, constituting the 18 source terms, $S(r_i)$, were modeled as isotropic point sources with 0.15 W output power. The partial current boundary condition was implemented at the boundaries:

$$\hat{n} \cdot D\nabla\phi_{ij} + \frac{1}{2}\left[\frac{1-R_{\it eff}}{1+R_{\it eff}}\right]\phi_{ij} = 0 \qquad (9)$$

For all boundaries, $R_{\it eff}=1$, except for the prostateurethra interface where Reff=0.493 to model an air-filled urethra. Equation (8) is solved 18 times, i.e. with one source fiber active at a time, resulting in the fluence rate distribution due to each of the 18 sources. In particular, the fluence rate at the positions of the six neighboring fibers is assessed as a means to quantify the light transmission between treatment fibers. In the clinical setting the input for the software module evaluating the effective attenuation coefficients consists of 18×6 transmission spectra from the spectrometers in the detection unit. These spectrometers cover the wavelength interval 630 to 840 nm, whereas the FEM simulations were only performed for one wavelength with optical properties chosen to match those at 652 nm, representing the therapeutic wavelength in the case of Temoporfinmediated PDT. Therefore, 18×6 full spectra were constructed by fitting a Gaussian function centered at 652 nm with a HWHM of 2 nm and a peak value given by the fluence rate from the FEM simulations. Furthermore, white Gaussian noise with a standard deviation equal to 0.1% of the maximum transmission signal was added to each spectrum to represent detector dark noise.

The FEM simulation process was performed for different levels of light absorption within the prostate. Table 4 lists the optical properties used in the simulations. For each simulation, spatial variations of the prostate tissue optical properties were modeled by adding white Gaussian noise with a SD of 10 and 5% of $\mu_a$ and $\mu_s'$, respectively. These noise data were generated for every fifth voxel within the geometry voxel model and was linearly interpolated to voxels in between. In this way spatial variations of the optical properties typically found in prostate tissue may be correctly modeled. These simulations thus provided data on the light transmission between treatment fibers to be used as input for the software module evaluating the effective attenuation coefficients. The possibilities of incorporating well defined and spatially varying absorption and scattering coefficients as well as tissue heterogeneities were the main motivations for choosing FEM simulated data on light transmission levels instead of experimental data within tissue phantoms.

TABLE 4

Optical properties used for the fluence rate simulations. All units are in [cm$^{-1}$].

|  | Prostate | Rectum | Urethra | Normal |
|---|---|---|---|---|
| $\mu_a$ | 0.3, 0.4, 0.5, 0.6, 0.7 | 0.3 | air-filled | 0.3 |
| $\mu_s'$ | 8.7 | 8 | air-filled | 8 |
| $\mu_{\it eff}$ | 2.8, 3.3, 3.7, 4.1, 4.4, 2.7 | 2.7 | air-filled | 2.7 |

Results

Below, the first two sections separately present results on the evaluation of target tissue optical properties and individual fiber irradiation times. In the subsequent section, the two software modules are combined, thus representing a real-time dosimetry module, also referred to as the IDOSE module, which is tested and verified on different simulated treatment scenarios.

Optical Properties

Light transmission data simulated by the FEM for five levels of light attenuation within the prostate were used as input for the software module developed for evaluating the effective attenuation coefficients. FIG. 8a shows the individual $\mu_{\it eff(i)}$ evaluated from the modeled data set for different levels of absorption 800 within the prostate 711. The FEM was utilized to provide data on light transmission signals within a realistic prostate geometry. Here, $\mu_s'$=8.7 cm-1 within the prostate for all simulations. In FIG. 8b the data have been averaged for the eighteen source fibers for each absorption level 820.

Here, markers 821 and error bars 822 represent the average $\mu_{\it eff}$ and ±1 SD, respectively. The dashed line 823 indicates the true $\mu_{\it eff}$ within the prostate. To investigate the influence of the heterogeneous geometry on the transmission measurements, a sensitivity analysis was performed. Considering absorbing heterogeneities, the change in the fluence rate at $r_j$ from a point source in $r_i$, i.e. $\phi_{ij}$, due to an absorption change in a voxel at $r_k$, i.e. $\Delta\mu_{a(k)}$ is given by:

$$\Delta\ln(\phi_{ij}) = J_{ijk}\Delta\mu_{a(k)} = -\frac{G_{ik}G_{kj}}{G_{ij}}\Delta\mu_{a(k)} \qquad (10)$$

Here $G_{ik}$ is the Green's solution to the diffusion equation, as stated in Equation (3), for the fluence rate in voxel k due an isotropic point source in location $r_i$. $G_{kj}$ and $G_{ij}$ are defined analogously and J is the Jacobian. Equation (10) was calculated in the FEM-mesh for all source-detector pairs. To quantify to what extent the transmission signals probe the target tissue and the different OAR, a fiber and tissue type-specific Jacobian was evaluated;

$$\tilde{J}_{i,B_s} = \sum_{k \in B_s} \sum_{j=1}^{6} J_{ijk} \quad i = 1, \ldots, 18 \qquad (11)$$

$B_s$ represents any of the tissue types included in the geometry and index j relates to the neighboring detection fibers, in the embodiment six neighboring detection fibers.

FIG. 9a is a bar 900 displaying $\tilde{J}_{i,B_s}$ normalized with respect to the total sum of the Jacobian for each treatment fiber. The relative error between the evaluated and the true $\mu_{\it eff}$ are also incorporated for completeness. The underestimation of the effective attenuation coefficient may for instance be explained by the presence of the air-filled urethra and the lower overall attenuation within the remaining organs, especially influencing light transmission between fibers close to either the urethra or the periphery of the prostatic gland. For most source fibers, a large error of the evaluated $\mu_{\it eff}$ corresponds to high $\tilde{J}$ for urethra and/or normal tissue.

FIG. 9b is a schematic graph 920 that displays $\tilde{J}$ summed in the z-direction for the monitoring subgeometries corresponding to fibers 6, 14 and 17. Here, fiber 6 probes mostly prostate tissue and correspondingly is associated with a small error of the evaluated $\mu_{\it eff}$. On the other hand, fibers 14 and 17 also detect light transmitted via normal, surrounding tissue and the urethra, leading to deteriorated estimations of the effective attenuation coefficient.

From FIG. 9a it can be observed that fiber 12 is associated with a much smaller error than fiber 14 despite having similar $\tilde{J}$ for urethra tissue. A more detailed analysis shows that for source fiber 14 it is the transmission signal to only one detection fiber that probes the urethra, whereas for fiber 12 the transmission to all six detection fibers probe the urethra to an equal but small extent. The linear fit performed to extract $\mu_{eff(i)}$ are thus characterized by different error values.

Figure 9:
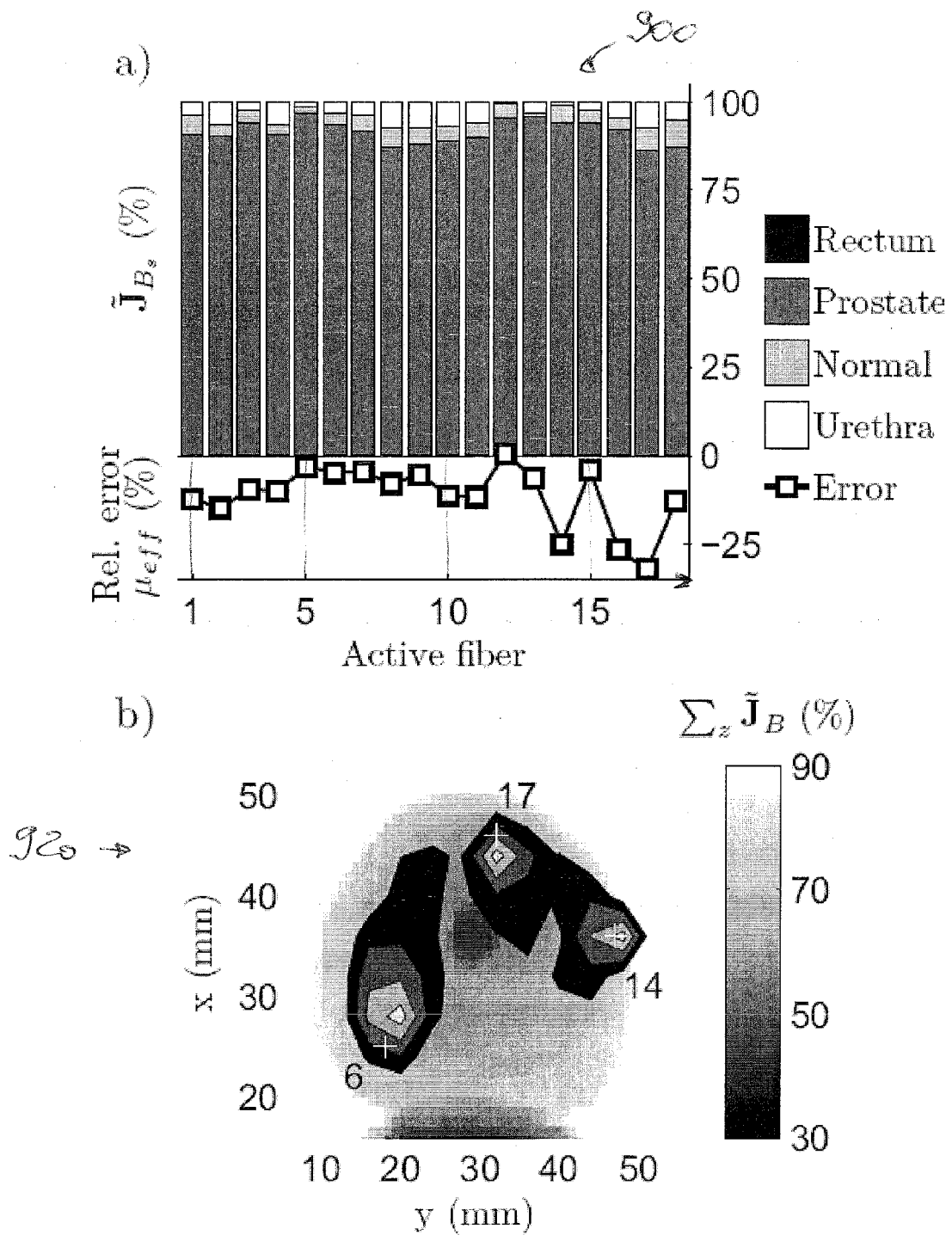
FIG. 9a is a bar plot showing a fiber and tissue type-specific Jacobian, normalized for each source fiber, together with the relative error of the evaluated between the evaluated and the true $\mu_{eff}$.
FIG. 9b is a schematic graph illustrating isosurfaces of summed Jacobians in z-direction for fibers 6, 14 and 17.

The probed tissue volumes depend on the tissue optical properties and in FIG. 9 $\mu_{eff}$=3.7 cm$^{-1}$ within the prostate gland. $\mu_{eff}$ was not underestimated when evaluating simulated data for a totally homogeneous medium. It was also observed that varying the SNR-threshold between 1 and 10 had negligible influence on the average $\mu_{eff}$.

B. Irradiation Times

Figure 10:
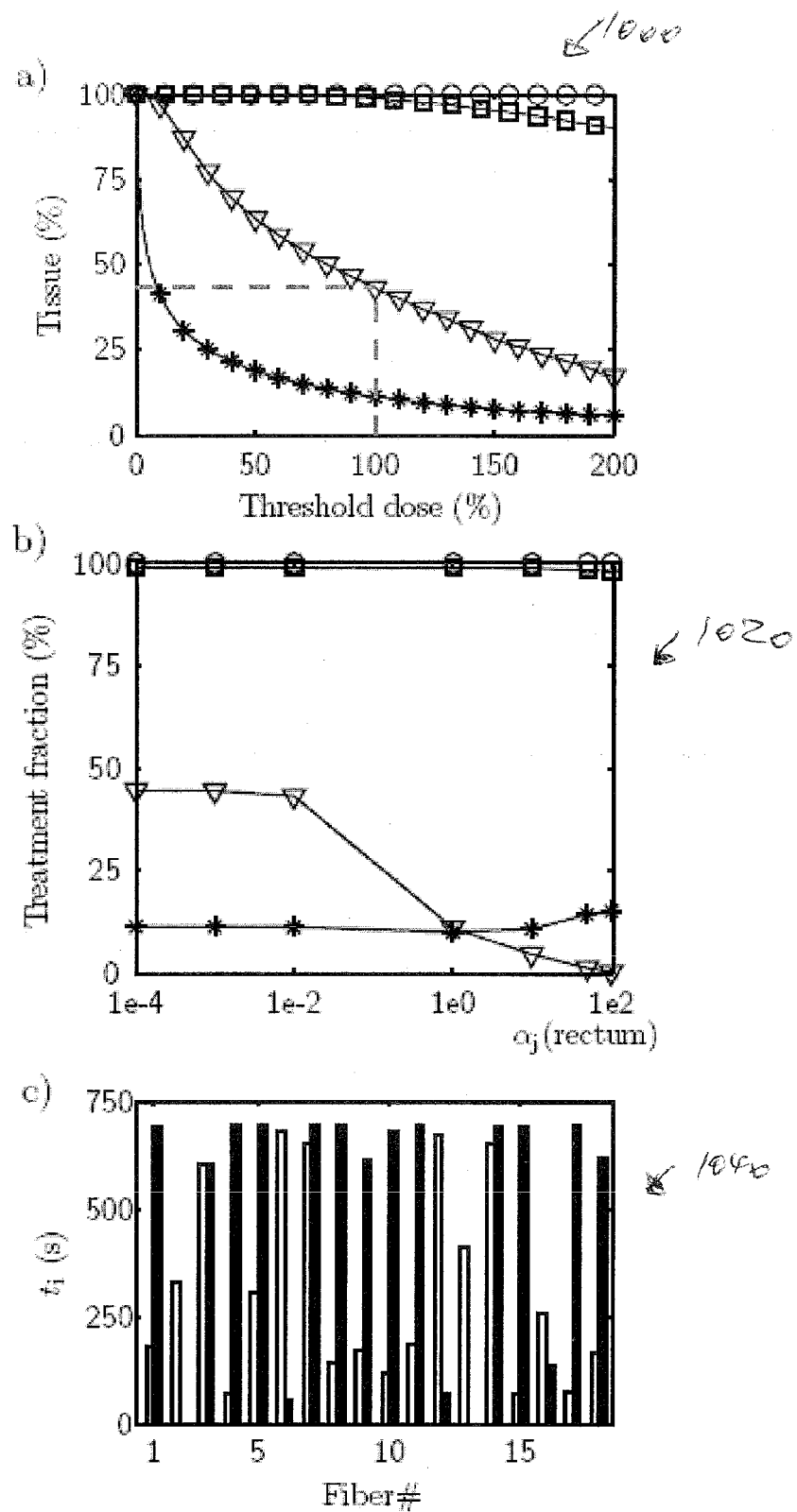
FIG. 10a is a graph illustrating dose volume histograms (DVHs) of the delivered light dose on the rectum, prostate, urethra, and normal tissue.
FIG. 10b is a graph illustrating a treatment fraction for each tissue type for varying $\alpha_j$(rectum)
FIG. 10c is a bar plot showing irradiation times for each source fiber for different $\alpha_j$(rectum)

The possibility of imposing varying sensitivity on the organs at risk (OAR) was investigated by studying the predicted irradiation times and delivered light doses after changing the importance weight on the rectum. As an example, FIG. 10a shows the dose volume histograms (DVHs) 1000 of the delivered light dose for an importance weight on the rectum of 0.01. The weights on the remaining organs remained fixed at values given in Table 3. For all calculations, $\mu_{eff(i)}$=3.7 cm$^1$ in the target tissue. All DVHs were calculated based on the irradiation times predicted by the Block-Cimmino optimization algorithm and the fluence rate as modeled by the FEM. The dashed lines are used to illustrate that approximately 43% of the rectum is exposed to the threshold light dose for this set of importance weights. The corresponding figure, hereafter referred to as the treatment fraction, is 98% for prostate tissue indicating that almost the entire gland is targeted for this set of importance weights.

The $\alpha_j$ (rectum) was then varied between 1e-4 and 500 and the treatment fraction for each tissue type is plotted 1020 in FIG. 10b.

For $\alpha_j$ (rectum) >1 the rectum is better discriminated from the target tissue and the treatment fraction of the prostate gland is still sufficiently large. In FIG. 10c the individual fiber irradiation times for $\alpha_j$ (rectum)=1e-4 (white bars) and 500 (black bars) are shown 1040. From this plot, two observations need to be emphasized. First, source fibers closer to the rectum, i.e. fibers 2, 6, 12, 13 and 16, are characterized by shorter irradiation times the higher the sensitivity on the rectum. Second, the irradiation times for source fibers positioned at the greatest distance from the rectum, i.e. fibers 1, 4, 5, 8, 11, 15, 17 and 18 positioned within the anterior part of the gland, are prolonged for the case of higher rectum importance weight. These effects are explained by the relatively high $\alpha_j$ on the prostate, always directing the Block-Cimmino optimization algorithm towards a solution that theoretically will treat as large fraction of the target tissue as possible. For the case of the highest importance weight on the rectum, the source fiber positions are most likely not optimal and thus fibers distant from the rectum are forced to deliver a much larger light dose. This helps explain the drastic increase of the total delivered light energy, defined as the sum of all fiber irradiation times multiplied by the 0.15 W output power used in this example, from 865 to 1350 J.

The total treatment time, as determined by the maximum irradiation time, is not greatly influenced by the varying importance weight. For a certain $\mu_{eff}$, the total treatment time is primarily determined by the geometry, i.e. the size of the target tissue as well as the source positions. Due to the 1/r exp($-\mu_{eff}r$) dependence of the fluence rate from an isotropic point source, the total treatment time increases rapidly with the glandular volume. For the remainder of the results, $\alpha_j$ (rectum) remains fixed at 5.

FIGS. 11a and 11b 1100 and 1120 respectively illustrate the consequences on the DVHs and irradiation times of increasing the absorption coefficient within the prostate. Here, $\mu_a$ were set to constant values of 0.3 (dotted), 0.5 (dash-dotted) or 0.7 (solid) cm−1 whereas $\mu'$ s=8.7 cm−1. Thus, $\mu_{eff(i)}$=2.8, 3.7 or 4.4 cm−1 was used as input for the Block-Cimmino optimization algorithm for all source fibers. All DVHs utilize FEM modeled data on the fluence rate. The DVHs in FIG. 11a indicate some overtreatment of the rectum as well as a larger treatment fraction of the prostate gland for the higher levels of light attenuation within the prostate. These effects are explained by the assumption of an infinite, homogeneous medium inherent in the current implementation of the Block-Cimmino optimization algorithm. Firstly, the lower absorption and scattering levels outside the prostate that were used in the FEM model causes the Block-Cimmino algorithm to underestimate the light propagation. The overtreatment is thus more pronounced the larger the difference of $\mu_{eff}$ between target tissue and OAR. Secondly, the increased target tissue treatment fractions for the higher absorption levels are due to the more rapid decay of the diffuse fluence rate with distance from a point source for increasing $\mu_{eff}$. From the expression $$\frac{\partial \phi}{\partial r} \propto \frac{\partial}{\partial r}\left[\frac{1}{r}\exp(-\mu_{eff}r)\right],$$

derived from Equation (4), it is evident that the transition zone between treated, i.e. light doses above the threshold, and untreated, i.e. light doses below the threshold, regions becomes more narrow the higher the effective attenuation coefficient. Thus, under the assumption of an infinite, homogeneous medium it is theoretically easier to discriminate between target tissue and OAR. This effect is particularly pronounced for large source distances, influencing the Cimmino optimization algorithm to also target the prostate periphery. In conclusion, increasing $\mu_a$ leads to better targeting of the prostate gland at the expense of overtreating OAR.

FIG. 11b illustrates the need for longer irradiation times for higher levels of target tissue absorption. For $\mu_a$=0.3 and 0.7 cm-1 the total light energy is approximately 420 and 1065 J, respectively. With increasing absorption, the relative increase in individual irradiation time is largest for fibers characterized by initially short irradiation times and located close to the rectum. Fibers characterized by the longest irradiation times are positioned in the peripheral regions of the prostate gland but further away from the rectum. However, the treatment time, as determined by the maximum irradiation time, is only increased by 90 s when going from the lowest to highest absorption level. This effect might be explained by the ability of the Cimmino optimization algorithm to converge to a close approximation of the least-intensity feasible solution in combination with the rapid decay of the fluence rate with distance from an isotropic point source. From the perspective of optimizing the treatment volume it is more "cost-effective" to distribute the higher light dose required among all treatment fibers instead of letting a few source fibers carry the load alone. This inevitably also introduces a spatial shift of the treated tissue volume for varying $\mu_{eff}$-levels.

C. IDOSE Module

During the actual treatment procedure, the effective attenuation coefficients are evaluated from light transmission data and used as input for the Block-Cimmino optimization algorithm to predict individual source fiber irradiation times.

This procedure was described in Section A and has been implemented in an effort to incorporate realtime treatment feedback in clinical IPDT on prostate tissue. In this section, the performance of the IDOSE module, i.e. steps (8) and (9) in FIG. 16, is verified on treatment scenarios displaying both temporally invariant and varying target tissue optical properties. As in the section "optical properties", light transmission signals obtained from the FEM simulations were utilized as input for the module evaluating the target tissue optical properties. The resulting DVHs were calculated based on total irradiation times as calculated by the IDOSE module and fluence rate distributions as modeled by the FEM.

Figure 12:
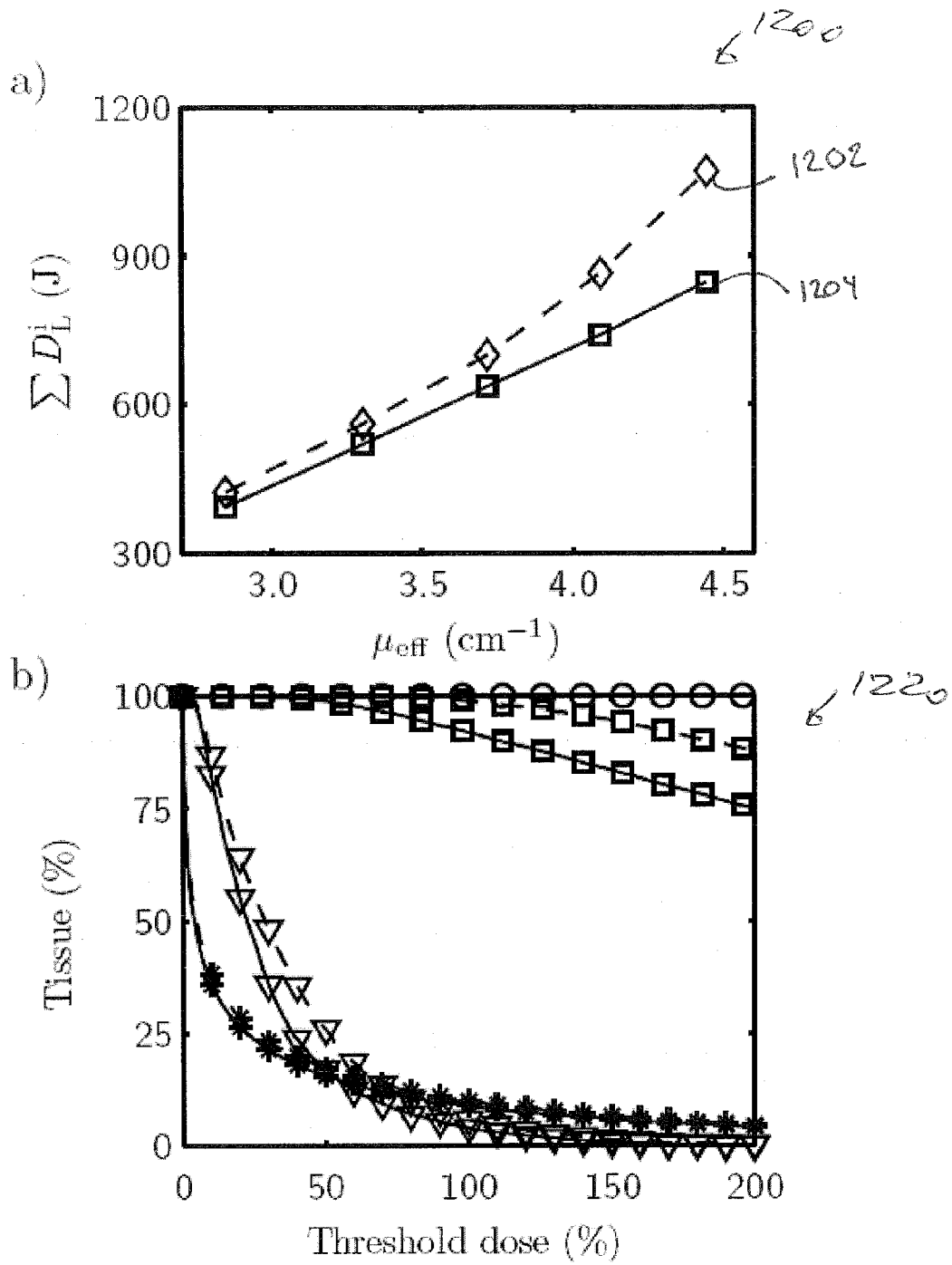
FIG. 12a is a graph illustrating a total light energy for different levels of light attenuation within the prostate.
FIG. 12b is a graph illustrating dose volume histograms (DVHs) of the delivered light dose corresponding to the true and evaluated effective attenuation coefficients.

FIG. 12a shows the total light energy predicted by the Block-Cimmino optimization algorithm as a function of the prostate $\mu_{eff}$ assuming this coefficient remains constant throughout the entire treatment session in graph 1200. The total light energy, obtained by summing the fiber irradiation times and multiplying by the 0.15 W output power, is shown both for the true, i.e. the effective attenuation coefficient used in the FEM simulations, (diamond markers) 1202 and evaluated (square markers) $\mu_{eff(i)}$ 1204. The graph illustrates a dramatic increase in light energy, and thus total irradiation times, with higher overall absorption.

Figure 8:
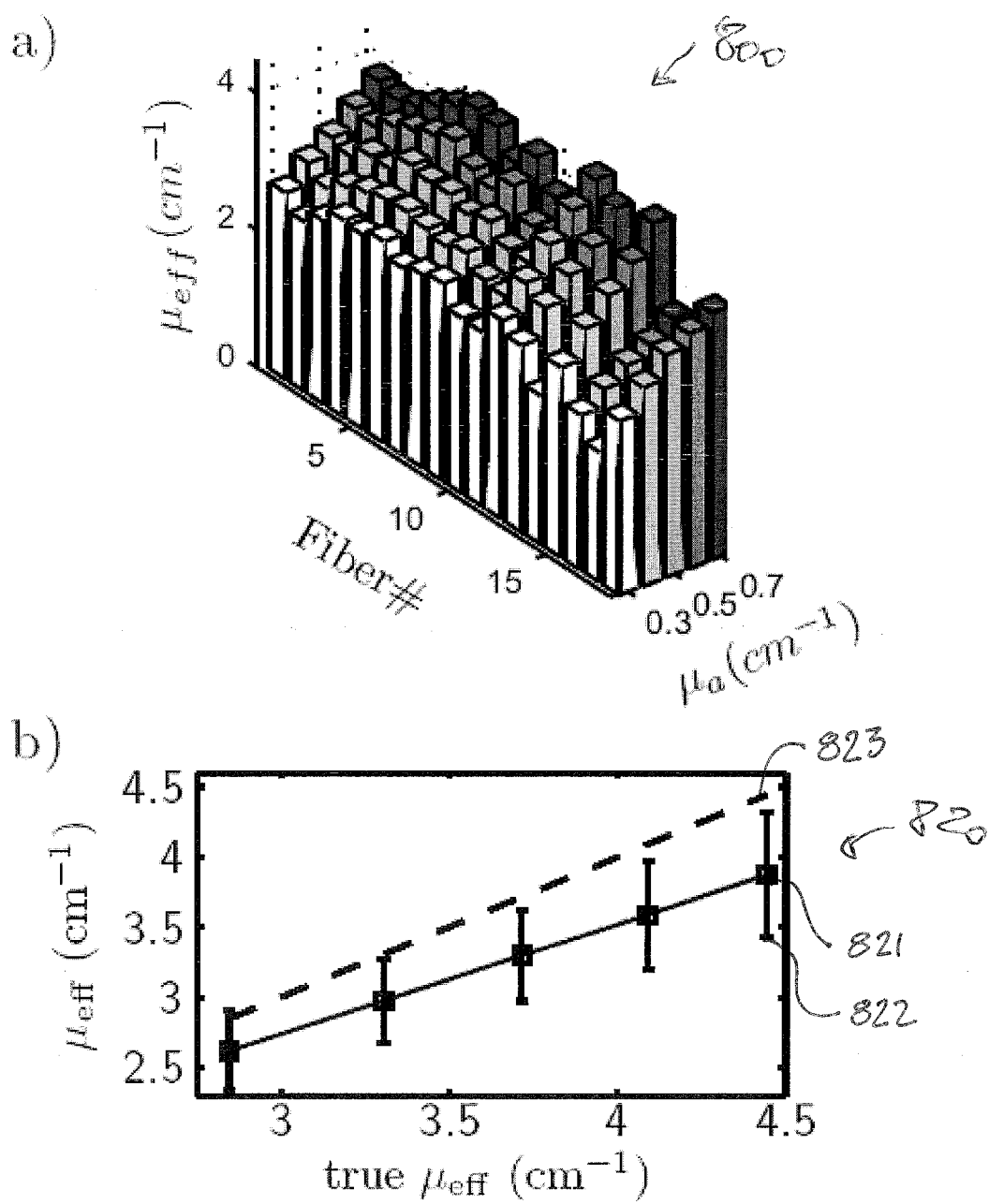
FIG. 8a is a 3D graph that shows individual $\mu_{eff(i)}$ evaluated from the modeled data set shown in FIG. 7b.
FIG. 8b is a graph illustrating averaged data for eighteen source fibers for each absorption level.

The underestimation of $\mu_{eff}$, as already shown in FIG. 8, results in a decreased demand on total light energy as shown by the square markers. This effect is more pronounced for the higher $\mu_{eff}$-levels. FIG. 12b compares the DVHs of the delivered light dose for a true $\mu_{eff}=3.7$ cm$^{-1}$ in graph 1220. Dashed and solid lines correspond to true and evaluated $\mu_{eff}$, respectively, indicating a lower prostate treatment fraction resulting from underestimating the light attenuation coefficient. On the other hand, the treatment fractions of the remaining organs are rather insensitive to the error associated with the $\mu_{eff}$-evaluation. The influence on the prostate treatment fraction caused by underestimating the light attenuation can be decreased by increasing the target tissue importance weight (data not shown).

The IDOSE module was also verified on a treatment scenario displaying temporally varying $\mu_{eff}$. For these simulated treatment sessions, measurement sequences are performed after 0, 2, 4, 9 . . . min of therapeutic irradiation in order to match a realistic clinical treatment procedure. Following each measurement sequence, the $\mu_{eff(i)}$ are evaluated from FEM modeled light transmission signals and used as input for the Block-Cimmino algorithm.

Thus, individual fiber irradiation times are updated following each measurement sequence. This procedure is iterated until the remaining treatment time as predicted by the Block-Cimmino module equals zero.

Figure 13:
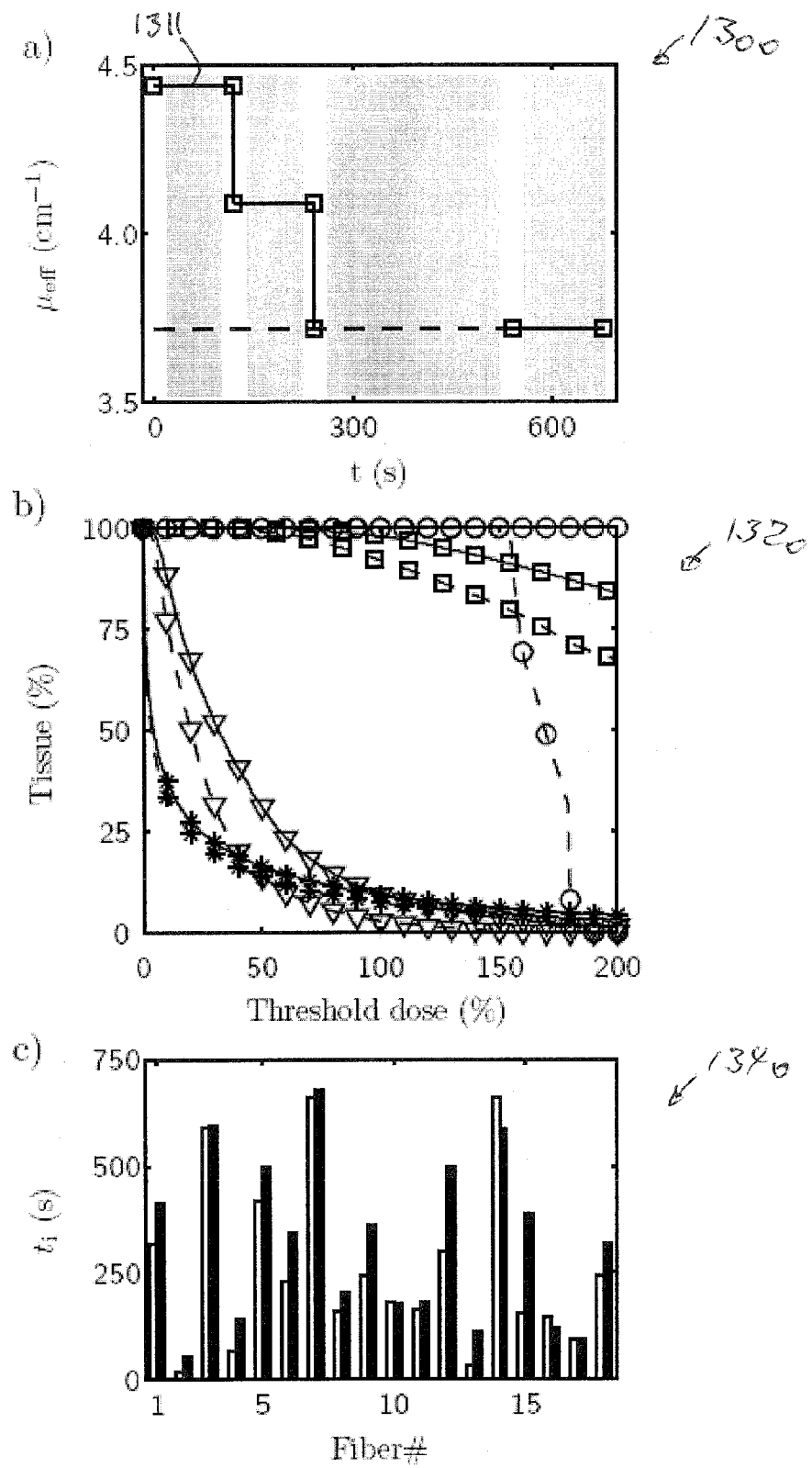
FIG. 13a is a graph illustrating $\mu_{eff}$ during the simulated treatment session compared to the default effective attenuation coefficient used for the pre-treatment plan.
FIG. 13b is a graph illustrating dose volume histograms (DVHs) of the delivered light dose without and with treatment feedback.
FIG. 13c is a graph illustrating irradiation times for each source fiber without and with feedback.

The time dependent $\mu_{eff}$ is indicated by the solid line 1311 graph 1300 in FIG. 13a. Such a situation might correspond to an initial increase in average blood content that gradually decreases as the blood flow is limited by the vascular effects of the PDT treatment. In the graph, the shaded areas indicate treatment sequences. The dashed line represents the default effective attenuation coefficient upon which the pre-treatment plan, i.e. steps (3) and (5) in FIG. 6, is based.

FIG. 13b compares the resulting DVHs of the delivered light dose for the cases of no treatment feedback 1320, i.e. irradiation times as predicted by the pre-treatment plan, (dashed lines) and with treatment feedback (solid lines) based on light transmission signals and evaluated $\mu_{eff(i)}$. The treatment fraction of the target tissue is larger for the case of treatment feedback (~98%) as compared to no treatment feedback (~91%).

Finally, FIG. 13c shows the fiber irradiation times without (white bars) and with (black bars) treatment feedback 1340. The higher absorption increases the demand on total light energy and causes prolonged irradiation times for most fibers. However, the feedback sets shorter irradiation times for source fibers 10, 14, 16 and 17, an effect that is explained by the $\mu_{eff}$-underestimation of these fibers as was illustrated in FIG. 8a.

In summary, a method and system for a treatment procedure for IPDT is provided in an embodiment for prostate tissue, incorporating realtime treatment monitoring and feedback based on a light dose threshold model. Algorithms have been implemented that utilize light transmission signals between treatment fibers in order to assess the effective attenuation coefficient within the target tissue. The calculated attenuation coefficients are then utilized as input for a Block Cimmino optimization algorithm, thus updating individual fiber irradiation times. By iterating such measurement sequences during the entire treatment session, the delivered light dose is individualized and compensated for treatment-induced alterations of the light attenuation within the target tissue.

To verify the performance of the realtime dosimetry module, the FEM was utilized to model the diffuse light distribution within a prostate model as realistic as possible. The model geometry used includes an air-filled urethra, lower levels of absorption and scattering within tissue surrounding the prostate as well as local variation in the prostate tissue optical properties. In addition, the use of the FEM was essential in evaluating the true DVHs from the predicted irradiation times in each treatment scenario.

As is demonstrated in FIG. 8, the $\mu_{eff}$-increase could be tracked but it was consistently underestimated. This effect was explained by the fact that the transmission signals for some source-detector fiber configurations also probed the urethra, which was modeled as air-filled, or the normal, surrounding tissue, characterized by lower levels of absorption and scattering. The method of spatially-resolved spectroscopy tends to average the effect of any heterogeneity throughout the entire tissue volume probed by the transmitted light.

One conclusion to be drawn from these results is that the prostate gland is small enough to allow surrounding organs to influence the diffuse light distribution. When relying on spatially resolved spectroscopy and diffuse light propagation for assessing the target tissue optical properties, one should be aware of these effects. Furthermore, as could be observed from the DVHs in FIG. 12b, the underestimation of $\mu_{eff}$ caused a slight undertreatment of the prostate. However, when in the clinical situation the treatment of the entire prostate gland is deemed essential, the undertreatment may be reduced by increasing the importance weight on the target tissue.

The presence of other tissue heterogeneities, such as calcifications and local blood accumulation, constitutes a further challenge to the algorithm assessing $\mu_{eff}$. Due to the strong absorption by hemoglobin, light transmission signals to and from occluded fibers will be characterized by poor SNR. The SNR-threshold for including a transmission signal can be adjusted to exclude fibers with large amounts of blood in front of the fiber tips. When ignoring data from one fiber, the current algorithm instead includes more distant fibers for evaluating $\mu_{eff(i)}$, thereby averaging the level of light attenuation over larger volumes and making the procedure less sensitive to the presence of a few local heterogeneities. The SNR threshold may for instance be optimized by extended simulations and in vivo clinical data.

The Block-Cimmino optimization algorithm is used to solve for individual fiber irradiation times provided the requirement to deliver a pre-determined light dose to the target tissue while sparing surrounding, sensitive organs.

The importance weights, $\alpha_j$, were adjusted to reflect the relative sensitivity of the OAR. As can be seen in FIG. 10b, increasing the importance weight of the rectum lowered the light doses within this organ.

In this context, the urethra was not considered a particularly sensitive organ due to the transient periods of catheterization.

The shorter calculation times achievable when utilizing the analytical expression for $Ø_{ij}$ as compared to for example a FEM-based model are most important for the realtime feedback scheme outlined here.

Figure 11:
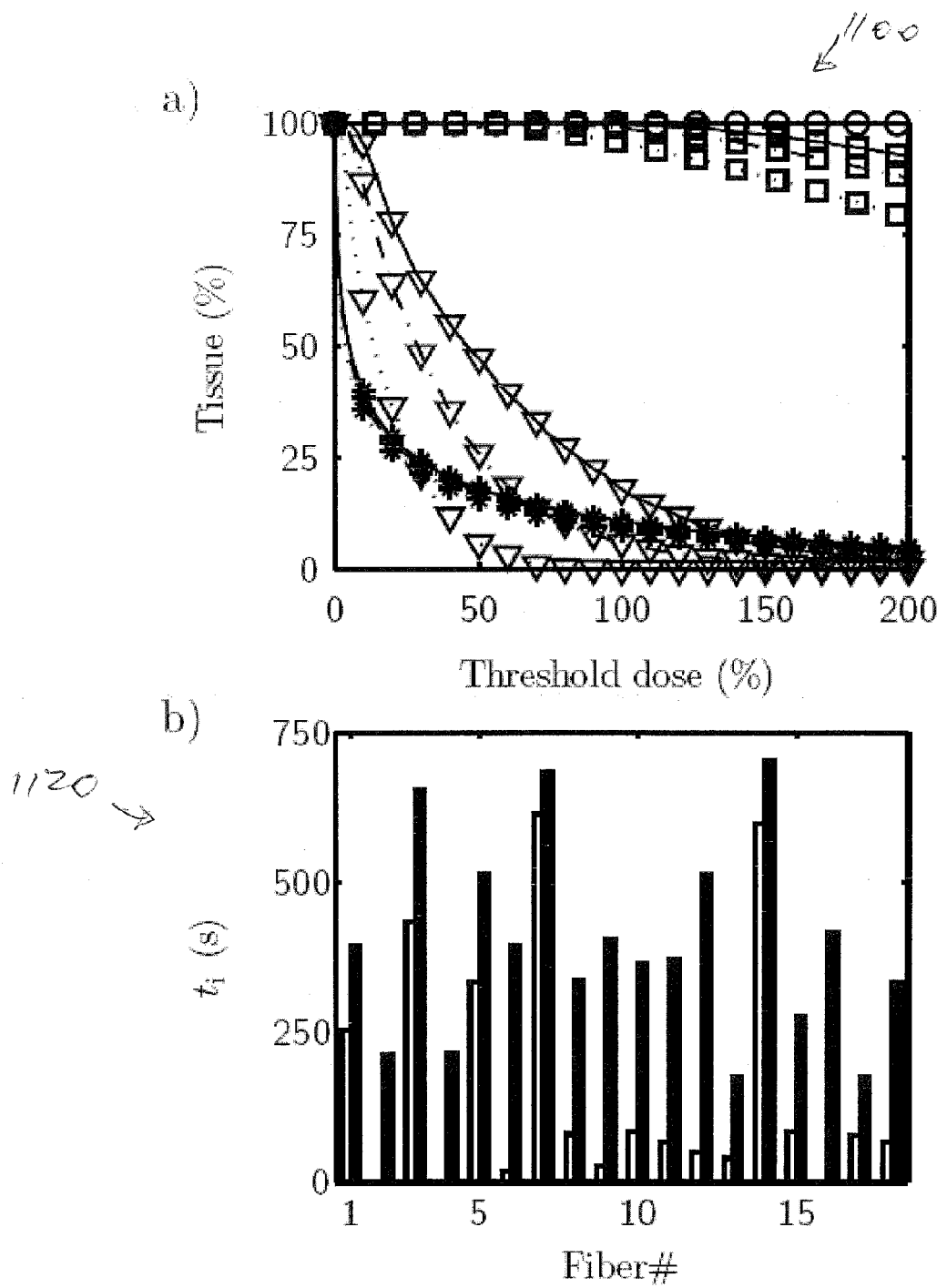
FIG. 11a is a graph illustrating dose volume histograms (DVHs) of the delivered light dose for varying absorption within the prostate gland.
FIG. 11b is a bar plot showing irradiation times for each source fiber for different $\mu_a$.

The influence on DVHs and irradiation times of varying the effective attenuation coefficient was studied in FIG. 11. Despite more than doubling the absorption coefficient, the treatment fraction of the prostate remained relatively constant, indicating a certain robustness of the Block-Cimmino algorithm. However, the higher the absorption within the prostate, the larger the treatment fraction of the OAR. This overtreatment is due to the assumption of an infinite, homogeneous medium, thus underestimating the light propagation within the organs surrounding the target tissue.

The concept of realtime treatment feedback was verified by executing the algorithms constituting the realtime dosimetry module on a simulated treatment session with temporally varying absorption. Here, the effective attenuation coefficient was significantly higher than usually observed within in vivo prostate tissue at the start of the treatment but was gradually decreased. For the case of no treatment feedback a pronounced undertreatment of the target tissue was noted. On the other hand, after enabling the realtime feedback, individual fiber irradiation times were adjusted so as to deliver a light dose exceeding the threshold dose to more than 90% of the target tissue voxels.

Thus, the ability of the IDOSE module to detect and compensate changes to the effective attenuation coefficient occurring during the IPDT procedure was shown.

As indicated by the treatment flow chart in FIG. 6, the evaluation of measured light transmission signals and updating of irradiation times are done in parallel to a treatment sequence. This procedure was implemented in order to limit total treatment times but also means that updating the irradiation times lags one cycle as compared to the measurement sequences. Therefore, a slight overtreatment of some tissue regions might occur in the unlikely event that there is a drastic reduction of the light attenuation at the end of a treatment session.

The software modules described in the context of this specification are implemented on a clinically adapted system for IPDT, and in an embodiment on prostate tissue. The IPDT apparatus is presented with a graphical user interface where the urologist is guided through all treatment steps indicated in FIG. 6 as well as a pre-treatment calibration procedure.

Furthermore, the software package constituting the realtime dosimetry module allows for high flexibility. First, a light dose escalation study may be carried out by changing the threshold dose. Secondly, a more or less aggressive treatment may easily be realized by adjusting individual tissue importance weights. Finally, any prior knowledge on tissue regions that need to be specially targeted may be incorporated into the Block-Cimmino algorithm by increasing their respective importance weight.

In this embodiment, dosimetry model is utilized based on the light dose only. Although this simplified model is most often clinically used, extensive research has demonstrated the importance of also including parameters such as the sensitizer concentration and the tissue oxygenation within the target tissue.

The IPDT apparatus also monitors a photosensitizer agent concentration, e.g. the Temoporfin fluorescence, and the tissue absorbance within the near-infrared wavelength region during the measurement sequences.

The PDT dose model may be extended to also incorporate the photosensitizer distribution and the target tissue oxygen saturation level. For example, fluorescence and near-infrared transmission signals may be combined with low-resolution optical diffuse tomography to map the spatial distribution of the sensitizer and tissue oxygenation levels. These parameters may then be weighted into the Block-Cimmino algorithm, for example increasing the demand on therapeutic light for regions with a lower photosensitizer concentration and pausing the treatment within hypoxic tissue volumes.

In conclusion, a method and system is presented that constitute a realtime dosimetry module for IPDT, in an embodiment on the whole prostate glandular tissue. Implemented on an 18 fiber IPDT apparatus, the dosimetry software includes monitoring of the light attenuation during the treatment procedure and updating individual fiber irradiation times. Thus, the delivered light dose may be adjusted to take into account patient-specific and treatment-induced variations in tissue light transmission during the treatment itself. Utilizing data on light distribution simulated by the FEM within a realistic prostate model have shown that increasing levels of light attenuation may be tracked. The Block-Cimmino algorithm is shown to predict irradiation times such that sufficiently large prostate volumes were targeted irrespective of the tissue optical properties. Finally, by continuously monitoring the tissue light transmission and updating irradiation times during a simulated treatment session, an undertreatment, evident for the case of no treatment feedback, is avoided.

As will be appreciated by one of skill in the art, the present invention may be embodied as device, system, method or computer program product. Accordingly, the present invention may take the form of an entirely hardware embodiment, a software embodiment or an embodiment combining software and hardware aspects all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices.

Embodiments of the present invention are described herein with reference to flowchart and/or block diagrams. It will be understood that some or all of the illustrated blocks may be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

It is to be understood that the functions/acts noted in the diagrams may occur out of the order noted in the operational illustrations. For example, two blocks shown in succession may in fact be executed substantially concurrently or the blocks may sometimes be executed in the reverse order, depending upon the functionality/acts involved. Although some of the diagrams include arrows on communication paths to show a primary direction of communication, it is to be understood that communication may occur in the opposite direction to the depicted arrows.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

The invention claimed is:

1. A system for providing interstitial photodynamic therapy on tissue in a body, said system comprising:
   at least one therapeutic light source;
   a plurality of optical fibers for delivering a therapeutic light from said at least one therapeutic light source to said tissue for interaction with a photosensitizer agent in said tissue, wherein said plurality of optical fibers are devised to be interstitially inserted into said tissue with a distal end region thereof;
   a diagnostic light source adapted to be coupled to a first optical fiber of said plurality of optical fibers to form a source fiber for delivering diagnostic light to said tissue while second and third fibers of said plurality of optical fibers neighboring said source fiber are employed as detector fibers;
   a device for evaluating at least one of a plurality of photodynamic treatment parameters of said interstitial photodynamic therapy at said distal end region of said optical fibers based on detected light from selected detection fibers of said plurality of optical fibers;
   a device for modifying characteristics of said therapeutic light of said interstitial photodynamic therapy in response to the evaluation of said plurality of photodynamic treatment parameters; and
   a control device that is arranged to restrict said delivery of therapeutic light treatment at least temporarily, for at least one optical fiber of said plurality of optical fibers, in dependence of at least one attribute of one of said plurality of photodynamic treatment parameters.

2. The system according to claim 1, wherein said control device is arranged to reduce said delivery of therapeutic light treatment at least temporarily without stopping it completely.

3. The system according to claim 1, wherein said control device is arranged to stop said delivery of therapeutic light treatment at least temporarily.

4. The system according to claim 1, wherein said control device is a regulator based on a difference between an actual value and a desired value of one of said plurality of photodynamic treatment parameters.

5. The system according to claim 1, wherein said control device is a thresholding device and said attribute is at least one threshold value of a value (P) of said one of said plurality of photodynamic treatment parameters.

6. The system according to claim 5, wherein said at least one threshold value comprises a first threshold (th1), a second threshold (th2), and a third threshold (th3), wherein said third threshold (th3) is lower than said second threshold (th2) and said second threshold (th2) is lower than said first threshold (th1), wherein said first threshold (th1), said second threshold (th2), and said third threshold (th3) are dynamically adjustable during said interstitial photodynamic therapy.

7. The system according to claim 6, wherein said first threshold (th1), said second threshold (th2), and said third threshold (th3) are each a portion of an initial desired or measured value of said one of said plurality of photodynamic treatment parameters, respectively.

8. The system according to claim 7, wherein said thresholding device is arranged to stop said delivery of therapeutic light treatment when said value (P) of one of said plurality of photodynamic treatment parameters is below said third threshold value (th3) of said one of said plurality of photodynamic treatment parameters.

9. The system according to claim 8, wherein said one of said plurality of photodynamic treatment parameters is a concentration of said photosensitizer agent in said tissue.

10. The system according to claim 9, wherein said third threshold is a predefined portion of an initial concentration of said photosensitizer agent in said tissue.

11. The system according to claim 10, wherein said predefined portion is in the range of 5% to 15% of said initial concentration.

12. The system according to claim 6, wherein one of said plurality of photodynamic treatment parameters is oxygenation of said tissue, and wherein said
   thresholding device is arranged to at least temporarily interrupt or reduce the light treatment when said value (P) of said one of said plurality of photodynamic treatment parameters is below said second threshold value (th2) and above said third threshold value (th3), and wherein said
   thresholding device is arranged to resume said light treatment if the tissue oxygenation subsequently raises over said first threshold value (th1) of said one of said plurality of photodynamic treatment parameters.

13. The system according to claim 5, wherein said thresholding device is arranged to restrict said delivery of therapeutic light treatment at least temporarily when said value (P) of said one of said plurality of photodynamic treatment parameters is below said second threshold value (th2) and above said third threshold value (th3), and wherein said thresholding device is arranged to resume operation with unrestricted delivery of therapeutic light treatment when said value (P) of said one of said plurality of photodynamic treatment parameters subsequently is above said third threshold (th3).

14. The system according to claim 13, comprising a timer device arranged to start a timer upon stopping said delivery of therapeutic light treatment at least temporarily when said value (P) of said one of said plurality of photodynamic treatment parameters is below said second threshold value (th2), and arranged to stop said delivery of therapeutic light treatment ultimately upon said timer exceeding a dynamically adjustable time value.

15. The system according to claim 1, wherein said device for modifying said characteristics of said therapeutic light is configured to provide said modification substantially in real time.

16. The system according to claim 15, wherein
   said photodynamic treatment parameter is a parameter related to a status of said tissue or of a photosensitizer agent in said tissue.

17. The system according to claim 5, wherein said thresholding device comprises
- a device for calculating a light dose distribution from measured parameters and time and power for each of said at least one therapeutic light source during a time interval from said parameters and said at least one threshold value;
- wherein said diagnostic light source and said device for calculating a light dose distribution are operatively connected and arranged for repeating said calculating until at least one of said parameters has reached a predetermined level, and thereupon terminating said photodynamic treatment parameter at least temporarily, for at least one optical fiber of said plurality of optical fibers.

18. The system according to claim 15, wherein
- said at least one therapeutic light source devised for said interstitial photodynamic therapy is arranged to provide said therapeutic light interstitially to said tissue via said plurality of optical fibers, and
- a device for controlling the light dose and/or temporal emission of illumination of said therapeutic light from said at least one therapeutic light source.

19. The system according to claim 1, wherein
- said photodynamic treatment parameter is an effective light attenuation coefficient of said tissue and said
- device for evaluating said photodynamic treatment parameter is a device for evaluating an effective light attenuation coefficient of said tissue during delivery of said therapy; and wherein said
- device for modifying said characteristics of said therapeutic light is a device for modifying said characteristics of said therapeutic light in response to the evaluation of said effective light attenuation coefficient of said tissue.

20. The system according to claim 1, wherein said at least one of said plurality of photodynamic treatment parameters is comprised in the list of light fluence rate distribution, effective light attenuation coefficient of said tissue, oxygenation of said tissue, blood flow of said tissue, temperature of said tissue, or sensitizer concentration in said tissue.

21. The system according to claim 1, comprising a device for calculating a light dose distribution that is arranged to calculate a light dose from a light fluence rate distribution or an initial light power multiplied by the time in which the therapeutic light is turned on in said therapy light emitting source for said therapy.

22. The system according to claim 1, wherein said tissue is a tumor tissue.

23. The system according to claim 1, comprising a calculation device for determination of status of tissue during said treatment.

24. The system according to claim 1, wherein said device for evaluating at least one photodynamic treatment parameter of said interstitial photodynamic therapy is arranged to stop said interstitial photodynamic therapy at said source fiber when a real or measured total light dose is delivered to said tissue at said distal end of said source fiber.

25. The system according to claim 1, comprising a device for tissue importance weighting within a Block-Cimmino algorithm arranged for discriminating between said tissue and organs at risk (OAR) adjacent said tissue in terms of deposited light dose.

* * * * *